(12) United States Patent
Gupta et al.

(10) Patent No.: US 8,212,076 B2
(45) Date of Patent: Jul. 3, 2012

(54) PREVENTION OF CELLULAR SENESCENCE IN MAMMALS BY NATURAL PEPTIDE COMPLEXES

(75) Inventors: Shyam K Gupta, Scottsdale, AZ (US); Linda Walker, Cardiff, CA (US)

(73) Assignee: Covalence, Inc., Chandler, AZ (US)

( * ) Notice: Subject to any disclaimer, the term of this patent is extended or adjusted under 35 U.S.C. 154(b) by 0 days.

(21) Appl. No.: 13/084,709

(22) Filed: Apr. 12, 2011

(65) Prior Publication Data

US 2011/0190202 A1 Aug. 4, 2011

Related U.S. Application Data

(63) Continuation-in-part of application No. 11/309,437, filed on Aug. 4, 2006, now Pat. No. 7,427,690, and a continuation-in-part of application No. 13/015,805, filed on Jan. 28, 2011.

(51) Int. Cl.
*C07C 229/08* (2006.01)
*C07C 233/05* (2006.01)
*C07D 233/64* (2006.01)
*C07D 207/08* (2006.01)

(52) U.S. Cl. ...... 564/153; 562/450; 548/533; 548/338.1

(58) Field of Classification Search ............... None
See application file for complete search history.

(56) References Cited

OTHER PUBLICATIONS

Subasinghe et al J. Med. Chem., 1990, 33, 2734-2744.*
Berge et al. Journal of Pharmaceutical Sciences 1977, 66(1), 1-19.*
Von Gruenigen Abstract of: Journal of Immunological Methods, 1989, 125(1-2), 143-146.*
Anderson et al Bioorganic & Medicinal Chemistry 2007, 15, 6678-6686.*

* cited by examiner

*Primary Examiner* — Yevegeny Valenrod

(57) ABSTRACT

Preventing skin aging by targeting multiple causes by a single bullet is of primal scientific and consumer interest. A treatment based on compositions of compound (I) for cellular senescence to control cellular degradation offers such a solution to multiple skin ailments including skin degradation from cancer, diabetes, radiation treatments, chemotherapy, and sun-burn; mitochondrial dysfunction, age spots, acne, loss of cellular antioxidants, collagen loss, loss of skin pliability, loss of skin suppleness, skin wrinkles including fine lines, oxidation, damage from radiation, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, scalp dryness, skin depigmentation, intracellular dehydration, and combinations thereof;

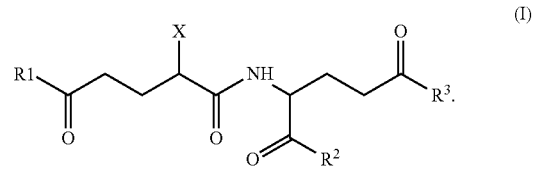

6 Claims, 2 Drawing Sheets

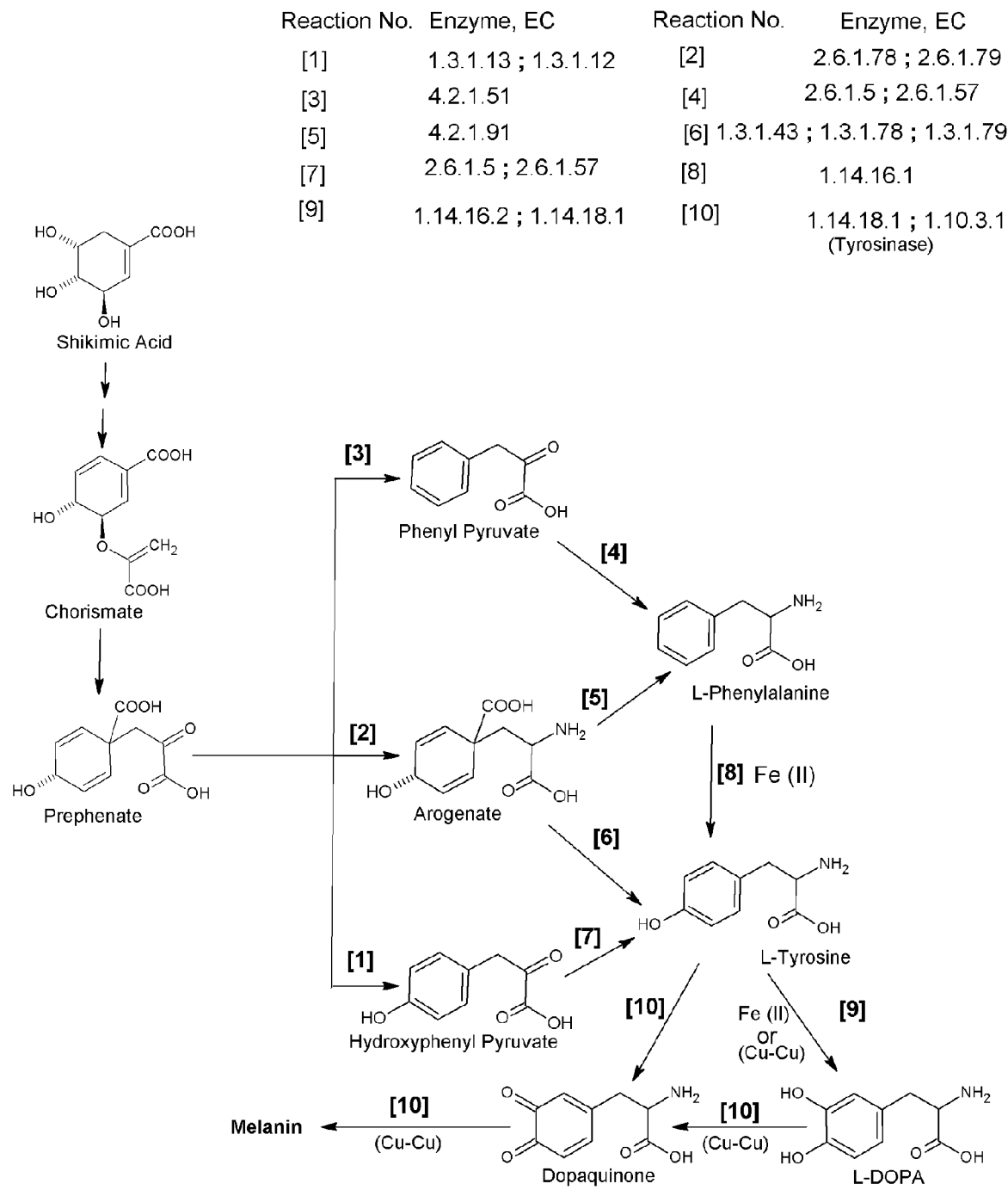
FIG. 1. L-Tyrosine & Melanin Biosynthesis via Shikimate Pathway

| Enzyme | Inhibition |
|---|---|
| Tyrosinase | + |
| Matrix Metalloproteases | + |
| Phenylalanine Oxidase | + |
| Catalase | - |
| Collagenase | + |
| Elastase | + |

FIG 2. Enzyme Inhibition Test.

PREVENTION OF CELLULAR SENESCENCE IN MAMMALS BY NATURAL PEPTIDE COMPLEXES

This invention is a continuation-in-part of U.S. patent application Ser. No. 11/309,437 (filed Aug. 4, 2006), now U.S. Pat. No. 7,427,690; and U.S. patent application Ser. No. 13/015,805 (filed Jan. 28, 2011).

BACKGROUND OF THE INVENTION

Cells are the fundamental structure composing our bodies, and cellular decline thus contributes to the aging process. Senescence or biological aging is the change in the biology of an organism as it ages after its maturity. Such changes range from those affecting its cells and their function to that of the whole organism.

This invention relates to certain amides of amino acids, peptides, and amino sugars. The compounds of the present invention possess cellular anti-senescence properties, which are suitable for topical or oral application for the treatment of ailments related to cell degradation caused by such cellular senescence, which include acne, rosacea, topical wounds, dandruff, skin disfigurements, age spots, wrinkles and fine lines, excess facial oil, and veterinary problems that result from intra-cellular dehydration and concomitant onset of intra-cellular inflammation including activation/inactivation of matrix metalloproteases (MMP), tyrosinase, proteasomes, and other enzymes in mammals.

DESCRIPTION OF THE RELATED ART

Wang et al. (FEBS Lett. 2011 Apr. 6; 585(7):986-94) report ageing in mammals remains an unsolved mystery. Anti-ageing is a recurring topic in the history of scientific research. Lifespan extension evoked by Sir2 (Silent information regulator S2) protein in lower organisms has attracted a large amount of interests in the last decade. They review recent evidence supporting the role of a Sir2 mammalian homologue, SIRT1 (Silent information regulator T1), in regulating ageing and cellular senescence. The various signaling networks responsible for the anti-ageing and anti-senescence activity of SIRT1 have been discussed. In particular, a counter-balancing model involving the cross talks between SIRT1 and AMP-activated protein kinase (AMPK), another stress and energy sensor, is suggested for controlling the senescence program in mammalian cells.

Lo et al. (Cell Transplant. 2010 Nov. 5) report glucose reduction prevents replicative senescence and increases mitochondrial respiration in human mesenchymal stem cells.

Zhou et al., (Atherosclerosis, 2010 November; 213(1):92-101) disclose that angiotensin II (Ang II) is able to accelerate endothelial progenitor cells (EPCs) senescence through induction of oxidative stress. Calcitonin gene-related peptide (CGRP), a major neurotransmitter of the capsaicin-sensitive sensory nerves, protects endothelial function through down regulating the expression of NADPH oxidase and reactive oxygen species production and increasing the production of klotho.

Campaner et al., (Cell Cycle. 2010 Sep. 15; 9(18):3655-61) disclose Ras proteins induce senescence, while Myc proteins generally trigger apoptosis. Myc is in fact viewed as an anti-senescence oncogene, as it is a potent inducer of cell proliferation and immortalization, bypasses growth-inhibitory signals, and cooperates with Ras in cellular transformation.

Zhong et al. (Diabetes Res Clin Pract. 2010 July; 89(1):38-45 report endothelial dysfunction to be a key event in the onset and progression of atherosclerosis associated with diabetes. Increasing cell senescence may lead to endothelial dysfunction and contribute to vascular complications. L-arginine may have an anti-senescence effect and it might be a therapeutic agent for diabetic vascular complications.

Xie et al. (Pharmazie. 2009 November; 64(11):752-4) report effects of echinacoside, one of the phenylethanoids isolated from the stems of Cistanches salsa, a Chinese traditional herbal medicine, on human embryo lung fibroblastic cells. The results indicate that echinacoside could protect cells from DNA damage, suggesting that echinacoside has potential anti-senescence activity.

Zin et al., (Pharmazie. 2008 April; 63(4):321-3) studied the influence of dendroflorin, a potentially active compound extracted from Dendrobium nobile, on cell growth and cell cycles was assessed in a human embryo lung fibroblastic cell; the results suggest that dendroflorin is a potential candidate with anti-senescence activity.

Ikushima et al., (Biochem Biophys Res Commun. 2006 Jan. 20; 339(3):827-32) report Klotho-mutated mice manifest multiple age-related disorders that are observed in humans. A recent study suggested that Klotho protein might function as an anti-aging hormone in mammals. Klotho acts as a humoral factor to reduce $H_2O_2$-induced apoptosis and cellular senescence in vascular cells.

Afanasev (Oxid Med Cell Longev. 2010 March-April; 3(2):77-85) reports reactive oxygen species (ROS) superoxide and hydrogen peroxide perform important signaling functions in many physiological and pathophysiological processes. Cell senescence and organismal age are not exemptions. Aging-regulating genes p66shc, Sirtuin, FOXO3a and Klotho are new important factors which are stimulated by ROS signaling. It has been shown that ROS participate in initiation and prolongation of gene-dependent aging development. ROS also participate in the activation of protein kinases and extracellular signal-regulated kinase ERK, which by themselves or through gene activation stimulates or retards cell senescence. Different retarding/stimulating effects of ROS might depend on the nature of signaling species—superoxide or hydrogen peroxide. Importance of radical anion superoxide as a signaling molecule with "super-nucleophilic" properties points to the possibility of the use of superoxide scavengers (SOD mimetics, ubiquinones and flavonoids) for retarding the development of aging.

Lester (Plant Sci. 2000 Dec. 7; 160(1):105-112) reports activated oxygen free-radicals cause peroxidative damage to all membranes and hasten senescence. Polyamines (PAs) are effective scavengers of these free radicals produced by lipoxygenase and phospholipase-D.

Wang et al., (Biochemistry (Mosc). 2000 July; 65(7):869-71) report Carnosine is an endogenous free-radical scavenger. The latest research has indicated that apart from the function of protecting cells from oxidation-induced stress damage, carnosine appears to be able to extend the lifespan of cultured cells, rejuvenate senescent cells, inhibit the toxic effects of amyloid peptide (A beta), malondialdehyde, and hypochlorite to cells, inhibit glycosylation of proteins and protein-DNA and protein-protein cross-linking, and maintain cellular homeostasis. Also, carnosine seems to delay the impairment of eyesight with aging, effectively preventing and treating senile cataract and other age-related diseases. Therefore, carnosine may be applied to human being as a drug against aging.

Certain amides of amino acids and peptides have been reported to possess interesting biological properties. Notable examples follow.

Conjugates of certain amino acid amides have been disclosed to possess tyrosinase inhibitory benefits (Jin-mi Noh et al., Bioorganic & Medicinal Chemistry Letters, Volume 19, Issue 19, 1 Oct. 2009, Pages 5586-5589).

Monoterpene-based chiral n-amino acid derivatives have been prepared from natural sources (Szakonyi et al., Amino Acids. 2011 Mar. 30).

Bertinaria et al., (J Med. Chem. 2011 Jan. 27; 54(2):611-21), disclose synthesis and the physicochemical and biological characterization of a series of carnosine amides bearing on the amido group alkyl substituents endowed with different lipophilicity are described. All synthesized products display carnosine-like properties differentiating from the lead for their high serum stability.

Ueoka et al., (J Am Chem. Soc. 2010 Dec. 22; 132(50): 17692-4), disclose two cytotoxic peptides, yaku'amides A and B that were isolated from the marine sponge *Ceratopsion* sp. The growth inhibitory profile of yaku'amide A against a panel of 39 human cancer cell lines was clearly unique and distinguished from other anticancer drugs.

Acharya et al., (J Biomed Sci. 2010 Aug. 24; 17 Suppl 1:S35), report that when used in overdoses, acetaminophen (APAP) is a common cause of morbidity and mortality in humans. At present, N-acetylcysteine (NAC) is the antidote of choice for acetaminophen overdoses. Prompt administration of NAC can prevent the deleterious actions of APAP in the liver. In view of the similarities in antioxidant effects demonstrated by NAC, hypotaurine (HYTAU) and taurine (TAU) in this and other our laboratories, the present study was undertaken to compare these compounds for the ability to attenuate plasma and liver biochemical changes associated with a toxic dose of APAP.

Pandya et al., (J Biomed Sci. 2010 Aug. 24; 17 Suppl 1:S16), report Poly(ADP-ribose; PARP) is a NAD requiring, DNA-repairing, enzyme playing a central role in pancreatic beta-cell death and in the development of endothelial dysfunction in humans and experimental animals. PARP activation is also relevant to the development of complications of diabetes. Hence, agents capable of inhibiting PARP may be useful in preventing the development of diabetes and in slowing down complications of diabetes. A comparative study of the binding characteristics to and inhibitory potencies towards PARP and in vivo antidiabetogenic potencies of taurine (TAU), 3-aminobenzamide (3-AB) and nicotinamide (NIC) showed the inhibitory potency order being 3-AB>NIC=TAU.

Sakuma et al., (J Control Release. 2010 Dec. 1; 148 (2): 187-96), disclose that oligoarginines, which are known as cell-penetrating peptides, enhance the cellular uptake of poorly membrane-permeable bioactive molecules that are chemically conjugated to them. A novel polymer, oligoarginine-linked poly(N-vinylacetamide-co-acrylic acid), was prepared with the expectation that the polymers will enhance the cellular uptake of the bioactive molecules that are physically mixed with them. Oligoarginines were grafted onto the polymer backbone through the chemical reaction with acrylic acid functional groups.

Penetratin-1 (Derosssi et al., 1996, J. Biol. Chem. 271, 18188-18193) is a 16-amino acid peptide corresponding to the third helix of the homeodomain of Antennapedia protein. This peptide is able to translocate across biological membranes by an energy-independent mechanism and has been used successfully to internalize covalently attached peptides and oligonucleotides and to convey them to the cytoplasm and nucleus of many cell types. Szucova et al., (Phytochemistry. 2011 Feb. 25), disclose certain N9-substituted derivatives of kinetin as effective anti-senescence agents.

Park et al., (J Gen Virol. 2011 Feb. 16) disclose hepatitis B virus X protein overcomes cellular senescence provoked by all-trans retinoic acid in HepG2 cells.

Skulachev et al., (Biochimica et Biophysica Acta—Bioenergetics, Volume 1787, Issue 5, May 2009, Pages 437-461; Biochemistry (Moscow), 2008, Vol. 73, No. 12, pp. 1329-1342. Published in Russian in) Biokhimiya, 2008, Vol. 73, No. 12, pp. 1655-1670) have attempted to prevent senescence via a mitochondrial approach. Antioxidants specifically addressed to mitochondria have been studied to determine if they can decelerate senescence of organisms. For this purpose, a project has been established with participation of several research groups from Russia and some other countries. A new type of compounds comprising plastoquinone (an antioxidant moiety), a penetrating cation, and a decane or pentane linker has been synthesized. These look promising for treatment of senescence and age-related diseases.

BRIEF DESCRIPTION OF THE SEVERAL VIEWS OF THE DRAWINGS

FIG. 1. Melanin Biosynthesis via Shikimate Pathway.
FIG. 2. Enzyme Inhibition Test.

DETAILED DESCRIPTION

Preventing skin aging by targeting multiple causes by a single bullet is of primal scientific and consumer interest. Treatments based on cellular anti-senescence now offer this single solution to multiple skin ailments including skin aging!

Senescence is the change in the biology of an organism as it ages after its maturity, which range from those affecting its cells and their function to that of the whole organism. Senescence is not universal, and senescence is not observed in single-celled organisms that reproduce through the process of cellular mitosis. Cellular senescence in humans causes the cells to stop replicating themselves through the process of mitosis, thus resulting in cellular degradation over a period of time.

Water is a key element for life. However, some organisms have evolved an amazing adaptation (osmoprotection) that allows them to survive under complete dehydration conditions for months or years, until water is present again, at which time they resume their metabolism and growth. Anhydrobiosis ("life without water") is found throughout all biological domains, for example in several species of eubacteria, archea, some fungi, certain invertebrate species and "resurrection plants". Cellular anti-senescence agents act through compatible solutes to prevent cellular damage. Osmoprotection has recently been recognized as a new therapeutic methodology (Messmer, Ophthalmologe. 2007 November; 104 (11): 987-90). Cellular anti-senescence agents act through compatible solutes to prevent—at least in theory—a hyperosmolar condition from damaging the cellular function.

Cells must maintain an optimal balance of water to stay plump and healthy. Imagine a face drawn on a balloon and filled with water. The face will look plump and youthful as the water keeps pressure on the balloon's inside surface. But if the water were to slowly leak (osmosis) out of the balloon, the drawn face would increasingly look wrinkled, tired, saggy, and aged.

There are several reports suggesting that hyperosmolarity induces inflammation. Schwartz et al., (J Inflamm (Lond). 2009 Jun. 23; 6:21) have shown that there is a the link between hyperosmolarity and inflammation by assessing osmolarity values in vivo during inflammation and compared the inflammatory potential of different osmotic agents and studied the long-term consequences of hyperosmolarity on cell fate. The exposure of cells to the different compounds, whatever their molecular weight, has no effect on the secretion of cytokines as long as the osmolarity is below a threshold of 300 mOsm. Higher osmolarities result in the secretion of proinflammatory cytokines (Interleukin-8, Interleukin-6, Interleukin-1beta and Tumor Necrosis factor-alpha).

Abolhassani et al. (Inflamm Res. 2008 September; 57(9): 419-29) report that hyperosmolarity can induce pro-inflammatory cytokine responses. Inflammation appears to be the simple consequence of a shift of methylation of Protein Phosphatase 2A, which in turn activates Nuclear factor-kappa B (NF-kappaB). The production of inflammatory cytokines causes the acceleration of aging process.

Sarkar et al. (Cancer Lett. 2006 May 8; 236(1): 13-23. Epub 2005 Jun. 22) report that a direct relationship exists between aging and increasing incidences of chronic diseases. In fact, with most age-associated diseases individuals manifest an underlying chronic inflammatory state as evidenced by local infiltration of inflammatory cells, such as macrophages, and higher circulatory levels of pro-inflammatory cytokines, complement components and adhesion molecules. Consequently, treatment with anti-inflammatory agents provide symptomatic relief to several aging-associated diseases, even as remote as Alzheimer's or Parkinson's disease, indicating that chronic inflammation may play a substantial role in the pathogenesis of these disease states. The molecular mechanisms underlying this chronic inflammatory condition during cellular senescence is presently unclear. Cellular damage by oxygen free radicals is a primary driving force for aging and increased activation of redox-regulated transcription factors, such as NF-kappaB that regulate the expression of pro-inflammatory molecules, has been documented in aged animals/individuals versus their young counterparts. Human polynucleotide phosphorylase (hPNPase (old-35)), a RNA degradation enzyme shown to be upregulated during differentiation and cellular senescence, may represent a molecular link between aging and its associated inflammation. HPNPase (old-35) promotes reactive oxygen species (ROS) production, activates the NF-kappaB pathway and initiates the production of pro-inflammatory cytokines, such as IL-6 and IL-8. In these contexts, inhibition of hPNPase (old-35) may represent a novel molecular target for intervening in aging-associated chronic diseases.

Chambers et al. (J Clin Invest. 1987 March; 79(3): 731-7) disclose that human urine is cellular anti-senescence for enteric bacteria, permitting *E. coli* to grow with high concentrations of NaCl and other salts and even higher concentrations of sucrose and mannitol but not urea. Two major cellular anti-senescence compounds in urine have been identified: glycine betaine, and proline betaine. The presence of glycine and proline betaines in human urine may reflect a cellular anti-senescence role for the kidney.

Chambers et al. (J. Bacteriol. 1987 October; 169(10): 4845-7) further report that glycine betaine is believed to be the most active naturally occurring osmoprotectant molecule for *Escherichia coli* and other bacteria. It is a dipolar ion possessing a quaternary ammonimum group and a carboxylic acid group. To examine the molecular requirements for cellular anti-senescence activity, dimethylthetin was compared with glycine betaine. Dimethylthetin is identical to glycine betaine except for substitution of dimethyl sulfonium for the quaternary nitrogen group. Dimethylthetin was found to be about equally as effective as glycine betaine in permitting *E. coli* to grow in hypertonic NaCl, and both compounds were recovered almost completely from bacterial cells grown in the presence of hypertonic NaCl. 3-Dimethylsulfonioproprionate, an analog of dimethylthetin observed in marine algae, and 3-Dimethylsulfonio-2-methylproprionate was found to be less active. Dimethylthetin may prove useful as a molecular probe to study betaine metabolism and as a model for the development of antibacterial agents.

In modern medicine dry eye syndrome is one of the most common disorders encountered in daily ophthalmological practice. Hyperosmolarity of the tear film is one of the key pathogenetic factors in the development of a commonly subclinical inflammation of the ocular surface, the lacrimal gland and the tear film in dry eye syndrome. Cellular anti-senescence agents prevent a hyperosmolar tear film from damaging the ocular surface.

The agents that are known to provide osmoprotection in non-mammalian organisms and plants include trehalose, maltose, sucrose, palatinose, cellobiose, gentiobiose, turanose, sorbitol, calcium chloride, certain amino acids (such as proline and alpha-glutamate), alpha-D-mannopyranosyl-(1-->2)-alpha-D-glucopyranosyl-(1-->2)-glycerate, Di-myo-inositol 1,1'-phosphate, N(gamma)-acetyl-2,4-diaminobutyrate (NADA), ectoine, glycine betaine, carnitine, pipecolic acid, dimethylsulfoniopropionate, dimethylsulfonioacetate, peptones, taurine, and taltrimide.

While use of humectants and emollients has been a common practice, the application of osmoprotection in skin and hair care of mammals has so far been practically unknown.

Rosas-Rodriguez et al (Life Sci. 2010 Oct. 23; 87(17-18): 515-20; Epub 2010 Aug. 18) report enzymes involved in osmolyte synthesis, especially oxidative stress affecting osmoregulation in renal cells. Kidney medulla cells are exposed to a wide range of changes in the ionic and osmotic composition of their environment as a consequence of the urine concentrating mechanism. During antidiuresis NaCl and urea concentrations increase and an efficient urinary concentrating mechanism is accompanied by medullar hypoxia. Medullar hypotonicity increases reactive oxygen species, a byproduct of mitochondria during ATP production. High intracellular ionic strength, hypoxia and elevated ROS concentration would have deleterious effects on medulla cell function. Medulla cells respond to hypertonicity by accumulating organic osmolytes, such as glycine betaine, glycerophosphorylcholine, sorbitol, inositol, and taurine, the main functions of which are osmoregulation and osmoprotection.

Sagot et al. (Proc Natl Acad Sci USA. 2010 Jul. 13; 107 (28): 12652-7; Epub 2010 Jun. 22) report the dipeptide N-acetylglutaminylglutamine amide that was discovered in the bacterium *Sinorhizobium meliloti* grown at high osmolarity, and subsequently shown to be synthesized and accumulated by a few osmotically challenged bacteria.

Gouffi et al. (Int J Food Microbiol. 2000 Apr. 10; 55(1-3): 171-4; J Bacteriol. 1998 October; 180(19): 5044-51) report sucrose, trehalose, maltose, cellobiose, gentiobiose, turanose and palatinose are very unusual osmoprotectants for *Sinorhizobium meliloti*, because these compounds, unlike other bacterial osmoprotectants, do not accumulate as cytosolic osmolytes in salt-stressed *S. meliloti* cells. Rather, these compounds were catabolized during early exponential growth, and contributed to enhance the cytosolic levels of the two endogenously synthesized osmolytes: glutamate and the dipeptide N-acetylglutaminylglutamine amide.

Talibart et al. (Appl Environ Microbiol. 1997 December; 63(12):4657-63) report the fate of exogenously supplied glycine betaine and the dynamics of endogenous osmolytes that were investigated throughout the growth cycle of salt-stressed cultures of strains of *Sinorhizobium meliloti*, which differ in their ability to use glycine betaine as a growth substrate, but not as an osmoprotectant. Glycine betaine is only transiently accumulated as a cytoplasmic osmolyte, which virtually prevents the accumulation of endogenous osmolytes during the lag and early exponential phases of growth. Then, betaine levels in stressed cells decrease abruptly during the second half of the exponential phase. At this stage, the levels of glutamate and the dipeptide N-acetylglutaminylglutamine amide increase sharply so that the two endogenous solutes supplant glycine betaine in the ageing culture, in which it becomes a minor osmolyte because it is progressively catabolized. Ultimately, glycine betaine disappears when stressed cells reach the stationary phase.

Dominguez-Ferrera et al. (J. Bacteriol. 2009 December; 191(24): 7490-9; Epub 2009 Oct. 16) report the disaccharide trehalose is a well-known osmoprotectant, and trehalose accumulation through de novo biosynthesis is a common response of bacteria to abiotic stress.

Perez-Arellano et al. (Extremophiles. 2010 Jul.; 14(4): 409-15. Epub 2010 Jun. 11) report glutamate kinase, an enzyme involved in osmoprotection in plants and microorganisms, catalyses the first and controlling step of proline biosynthesis.

Lynch et al. (Biomaterials. 2010 Aug.; 31(23): 6096-103. Epub 2010 May 14) report a biopolymer that has been shown to facilitate efficient delivery of trehalose, a bioprotectant normally impermeable to the phospholipid bilayer, into ovine erythrocytes. Cellular uptake of trehalose was found to be dependent on polymer pendant amino acid type and degree of grafting, polymer concentration, pH, external trehalose concentration, incubation temperature and time.

Flanagan et al. (Nutr Metab (Lond). 2010 Apr. 16; 7:30) report topical application of carnitine in dry eye offers osmoprotection and modulates immune and inflammatory responses.

Kitko et al. (PLoS One. 2010 Apr. 8; 5(4): 10078) report diverse osmolytes including NaCl, KCl, proline, or sucrose contribute to cytoplasmic pH homeostasis in E. coli, and increase the recovery from rapid acid shift. Osmolytes other than K+ restore partial pH homeostasis in a strain deleted for K+ transport.

Iturriaga et al (Int J Mol. Sci. 2009 Sep. 1; 10(9): 3793-810) report trehalose, a non-reducing disaccharide, that is widely distributed in Nature and has been isolated from certain species of bacteria, fungi, invertebrates and plants that are capable of surviving in a dehydrated state for months or years and subsequently being revived after a few hours of being in contact with water. This disaccharide has many biotechnological applications, as its physicochemical properties allow it to be used to preserve foods, enzymes, vaccines, cells etc., in a dehydrated state at room temperature.

Jorge et al (FEBS J. 2007 June; 274(12): 3120-7. Epub 2007 May 22) report the discovery of a new solute, whose structure was established as alpha-D-mannopyranosyl-(1-->2)-alpha-D-glucopyranosyl-(1-->2)-glycerate (MGG). The level of MGG increased notably with the salinity of the growth medium up to the optimum NaCl concentration. At higher NaCl concentrations, however, the level of MGG decreased, whereas the levels of proline and alpha-glutamate increased about five-fold and 10-fold, respectively. MGG plays a role during low-level osmotic adaptation of Petrotoga miotherma, whereas alpha-glutamate and, to a lesser extent, proline are used for osmoprotection under salt stress. Fernandez et al (J. Bacteriol. 2010 March; 192(6): 1624-33. Epub 2010 Jan. 8) report that mannosylglucosylglycerate (MGG), recently identified in Petrotoga miotherma, also accumulates in Petrotoga mobilis in response to hyperosmotic conditions and supraoptimal growth temperatures.

Jung et al (J Membr Biol. 2006; 213(2): 119-33. Epub 2007 Apr. 6) report amino acid transport is a ubiquitous phenomenon and serves a variety of functions in prokaryotes, including supply of carbon and nitrogen for catabolic and anabolic processes, pH homeostasis, osmoprotection, virulence, detoxification, signal transduction and generation of electrochemical ion gradients.

Garcia-Estepa et al. (Syst Appl Microbiol. 2006 Dec.; 29(8): 626-33. Epub 2006 Feb. 15) report N(gamma)-acetyl-2,4-diaminobutyrate (NADA), the precursor of the compatible solute ectoine, to function as an osmoprotectant for the non-halophilic bacterium Salmonella enterica serovar Typhimurium.

Pintsch et al. (BMC Biochemistry 2002, 3:10) have shown that cells steadily face changes of the external osmolarity, to which they have to adapt. To withstand a steep increase in osmolarity, eukaryotic cells activate responses like "regulatory volume increase", accumulation of compatible osmolytes and stimulated expression of stress proteins. Recently, an exception from this scheme has been identified: Dictyostelium cells protect themselves against hyperosmolarity by largely rearranging cellular proteins, whereas no "regulatory volume increase", no accumulation of compatible osmolytes and no change of the expression pattern of the most abundant proteins were observed. Among the translocated proteins identified, cytoskeletal proteins appear to be predominant. In particular, the rearrangement of actin and myosin II to the cell cortex beneath the plasma membrane was shown to constitute a pivotal element of osmoprotection in Dictyostelium. In this process the distribution of the actin-associated protein Hisactophilin (a histidine rich; 31 histidine out of 118 amino acids) actin binding protein from Dictyostelium discoideum was investigated in order to gain a better insight into osmo-protective mechanism of the cell. Hisactophilin was found to be enriched in the cytoskeletal fraction of wild type cells exposed to hyperosmotic stress. Hisactophilin is both translocated to the cytoskeleton and phosphorylated during hyperosmotic stress in Dicytostelium.

Gupta (U.S. Pat. No. 7,427,690) discloses certain derivatives of amino acids and peptides with alkylarylketones having formula (I);

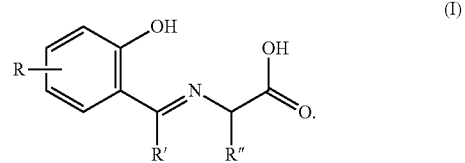

Gupta et al., (U.S. patent application Ser. No. 13/015,805) also disclose certain derivatives of amino acids, peptides, and amino sugars with another ketone, aloesin and isomers and salts thereof. For example, the reaction of aloesin with a dipeptide amide, glutamylglutamine amide, forms isomeric compounds of formula (II);

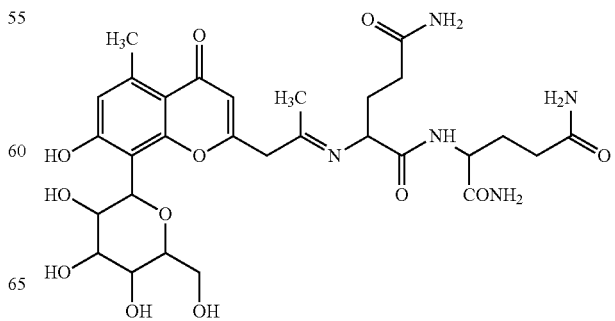

-continued

[Chemical structure]

The present invention is a continuation of the above discoveries, which now discloses composition comprising a compound of formula (III) that, surprisingly and unexpectedly, treat conditions of mammalian skin degradation resulting from cellular senescence:

(III)

[Chemical structure of formula (III)]

wherein,
R$^1$, R$^2$, and R$^3$ are selected from —OH, —NR$^4$R$^5$, amino sugar, and —OR$^6$; and
X is selected from —NH-peptide, —NH—C$^1$-C$^{20}$ alkanoyl, —NH-aroyl, —NR$^4$R$^5$, and —N=CR$^7$R$^8$; and
R$^4$ and R$^5$ are selected from H, alkyl, substituted alkyl, aryl, substituted aryl, heterocyclic, substituted heterocyclic, amino-alkanoyl, polyhydroxyalkyl, cycloalkyl, and amino sugar; and
R$^6$ is selected from H, and C$^1$-C$^{20}$ alkyl; and
R$^7$ and R$^8$ are selected from H, alkyl, substituted alkyl, aryl, substituted aryl, heterocyclic, and substituted heterocyclic; and
wherein said condition for skin degradation is from cancer, diabetes, radiation treatments, chemotherapy, and sunburn; mitochondrial dysfunction, age spots, acne, loss of cellular antioxidants, collagen loss, loss of skin pliability, loss of skin suppleness, skin wrinkles including fine lines, oxidation, damage from radiation, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, scalp dryness, skin depigmentation, intracellular dehydration, and combinations thereof.

The present invention also relates to compounds that are selective regulators of Ubiquitin-proteasome pathway, to cosmetic and pharmaceutical compositions containing them, and to their use in the prevention and/or treatment of ailments associated with the dysfunction of ubiquitin-proteasome pathway, including inflammation, wound healing, skin aging, body enzyme dysfunction, neurodegenerative disorders, and cellular apoptosis.

The examples of formula (III) include formula (IV);

(IV)

[Chemical structure of formula (IV)]; and formula (V), (V)

[Chemical structure of formula (V)]; and formula (VI), (VI)

[Chemical structure of formula (VI)]; and formula VII), (VII)

[Chemical structure of formula (VII)]; and formula (VIII);

(VIII)

[Chemical structure of formula (VIII)]; and of formula (IX), (IX)

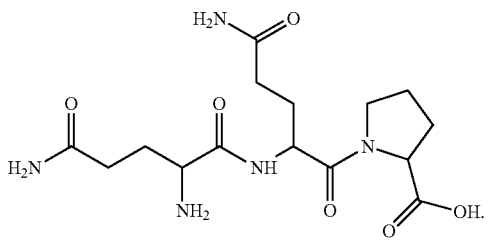

(X)

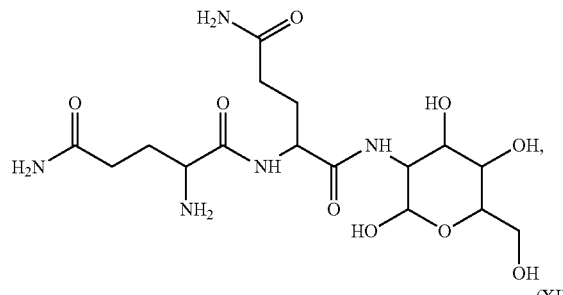

(XI)

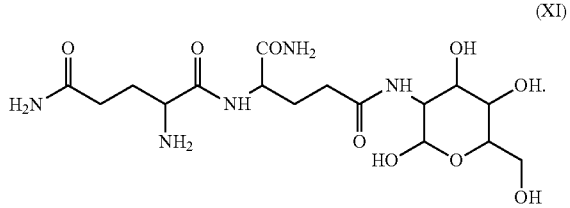

The present invention discloses a composition comprising a salt of the compound of formula (III), wherein said salt is a metal salt; said metal is selected from the group consisting of Li, Na, K, Ca, Mg, Ti, V, Cr, Mn, Fe, Co, Ni, Cu, Zn and Se.

The present invention discloses a composition comprising a salt of the compound of formula (III), wherein said salt is an acid salt; said acid is selected from the group consisting of inorganic and organic acids.

The present invention discloses a composition comprising a compound of formula (III) for pharmaceutical, nutraceutical, cosmetic, topical, or oral application.

The present invention discloses a composition comprising a compound of formula (III) to treat a condition of skin degradation selected from the group comprising challenged skin from cancer, diabetes, radiation treatments, chemotherapy, and sun-burn; mitochondrial dysfunction, age spots, acne, loss of cellular antioxidants, collagen loss, loss of skin pliability, loss of skin suppleness, skin wrinkles including fine lines, oxidation, damage from radiation, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, scalp dryness, skin depigmentation, intracellular dehydration, and combinations thereof.

The present invention discloses a method to treat a condition of skin degradation selected from the group comprising challenged skin from cancer, diabetes, radiation treatments, chemotherapy, and sun-burn; mitochondrial dysfunction, age spots, acne, loss of cellular antioxidants, collagen loss, loss of skin pliability, loss of skin suppleness, skin wrinkles including fine lines, oxidation, damage from radiation, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, scalp dryness, skin depigmentation, intracellular dehydration, and combinations thereof comprising administering an effective amount of a composition comprising a compound of formula (III).

For example, the derivatization of cellular anti-senescence compound, glutaminyl-glutamine amide with an amino sugar moiety provides cellular anti-senescence compounds of formula (X) and (XI), both of which having improved bioavailability;

The amino sugars suitable for similar derivatization with glutaminyl-glutamine amide and its variously substituted derivatives include, among others, glucosamine, galactosamine (chondrosamine), ribamine, allosamine, altrosamine, gulosamine, idosamine, talosamine, ribosamine, arabinosamine, xylosamine, lyxosamine, fructosamine, neuraminic acid (sialic acid), mannosamine, and their optical isomers.

The reaction of a β-amino acid, such as anthranilic acid, with a substituted glutaminyl-glutamine amide, for example, provides compounds of formula (XII) and (XIII);

(XII)

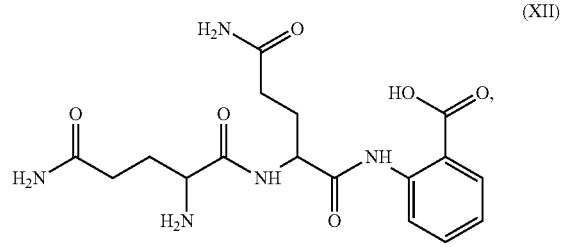

(XIII)

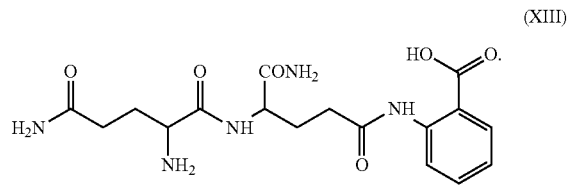

The present invention discloses a composition comprising a compound of formula (XIV);

(XIV)

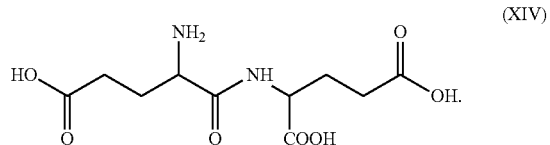

The present invention discloses a composition comprising a compound of formula (XV);

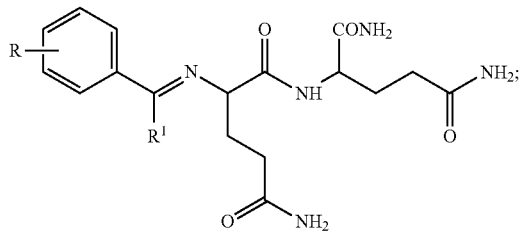

(XV)

wherein,
R is selected from H, OH, alkyl, substituted alkyl, halogen, oxyalkyl, and oxyaryl; and $R^1$ is selected from alkyl, substituted alkyl, aryl, substituted aryl, and heterocyclic.

The present invention discloses a composition comprising a compound of formula (XVI);

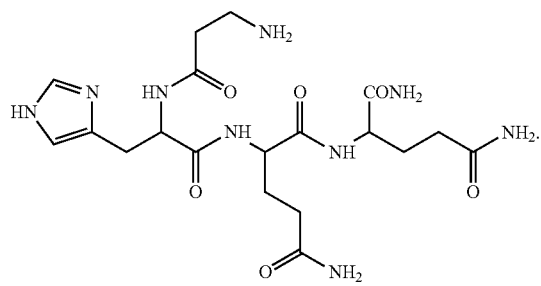

(XVI)

It is both surprising and unexpected that compounds of the present invention treat a condition of skin degradation selected from the group comprising challenged skin from cancer, diabetes, radiation treatments, chemotherapy, and sun-burn; mitochondrial dysfunction, age spots, acne, loss of cellular antioxidants, collagen loss, loss of skin pliability, loss of skin suppleness, skin wrinkles including fine lines, oxidation, damage from radiation, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, scalp dryness, skin depigmentation, intracellular dehydration, and combinations thereof. Although the exact mechanism of such treatment benefits is not known, it is believed to be a result of prevention of cellular senescence and moderation of ubiquitin-proteasome malfunction.

Ubiquitin-Proteasomes for Cellular Anti-Senescence.

The body constantly produces proteins and degrades proteins that are no longer needed or are defective. The production and destruction of proteins, called protein turnover, is a constant, ongoing process that is crucial for tissue renewal. A well-nourished person synthesizes nearly one pound of protein per day. Proteins that are broken down balance this protein gain. The process of protein breakdown, called proteolysis, is essential to cell survival. Numerous proteolytic systems exist in mammalian cells, the most important of which are the lysosomes, the ubiquitin-proteasome pathway, and enzymes called calpains. Lysosomes are small cell components that contain specific enzymes (proteases), which break down proteins. In the ubiquitin-proteasome pathway, proteins that are to be degraded are first marked by the addition of ubiquitin molecules and then broken down by large protein complexes called proteasomes. Calpains are proteases that are involved in several physiological processes, including the breakdown of proteins that give cells their shape and stability. The ubiquitin-proteasome system is now considered the major system involved in intracellular protein degradation. Two major components of this system are (1) three enzymes that add a small protein called ubiquitin onto substrate proteins destined for degradation, and (2) the proteasome, a rather large cellular particle composed of several smaller protein subunits, which executes the actual proteolysis. By degrading short-lived regulatory proteins, the ubiquitin-proteasome system controls basic cellular processes such as cell division, cell signaling, and gene regulation. The system also removes misfolded, damaged proteins, and in certain immune cells it breaks down foreign proteins into pieces called antigenic peptides, which can then be transported to the cell surface to induce an immune response [Ulrich, Current Topics in Microbiology and Immunology, vol 268, 137-174 (2002)].

Ubiquitin is a small protein that occurs in most eukaryotic cells. Its main function is to mark other intracellular proteins for destruction, known as proteolysis. Several ubiquitin molecules attach to the condemned protein (polyubiquitination), and polyubiquitinylated protein then moves to a proteasome, a barrel-shaped structure where the proteolysis occurs. Ubiquitin can also mark transmembrane proteins (for example, receptors) for removal from the membrane.

Ubiquitin consists of 76 amino acids with two sequentially linked glycine moieties at the carboxyl terminal and has a molecular mass of about 8500 amu. It is highly conserved among eukaryotic species: Human and yeast ubiquitin share 96% amino acid sequence identity.

The process of marking a protein with ubiquitin consists of a series of steps; (1) Activation of ubiquitin—the carboxyl group of the terminal glycine of ubiquitin binds to the sulfhydryl group —SH of an ubiquitin-activating enzyme E1. The sulfhydryl group is a cysteine residue on the E1 protein. This step requires an ATP molecule as an energy source and results in the formation of a thioester bond between ubiquitin and E1; (2) Transfer of ubiquitin from E1 to the ubiquitin-conjugating enzyme E2 via trans (thio) esterification; (3) Then, the final transfer of ubiquitin to the target protein can occur either directly from E2 (this is primarily used when ubiquitin is transferred to another ubiquitin already in place, creating a branched ubiquitin chain) or via an E3 enzyme, which binds specifically to both E2 and the target protein. The target protein is usually a damaged or non-functional protein that is recognized by a destruction-targeting sequence. Ubiquitins then bind to a lysine residue in the target protein via the transformation of thioester bond into an iso-peptide bond, eventually forming a tail of at least four ubiquitin molecules. The resulting ubiquitin-linked protein, called ubiquitin-protein conjugate, then can be recognized and degraded by the proteasome into peptides. This is the typical way to mark specific proteins for proteolysis. A functional proteasome (also called 26S proteasome) is composed of a smaller barrel-shaped core and two "caps" that are attached to the each end of the core. The proteasome core consists of four stacked rings containing two types of subunits, all facing into a central cavity. These subunits together have at least five distinct proteinase activities that cleave proteins at different sites. The "caps" at each end of proteasome perform a regulatory function. Each cap is composed of multiple subunits with numerous functions. These subunits recognize the ubiquitinylated protein, cut off the ubiquitin chains from this protein, thereby "unfolding" the protein, and open the channel inside the proteasome core so that the protein can enter the channel for degradation; and (4) Finally, the marked protein is digested in the 26S-proteasome into small peptides, amino acids (usually 6-7 amino acid subunits). Although the ubiquitins also enter the proteasome, they are not degraded (despite their protein structure) and may be used again.

Proteasomes are large multi-subunit protease complexes, localized in the nucleus and cytosol, which selectively degrade intracellular proteins. Proteasomes play a major role in the degradation of many proteins that are involved in cell cycling, proliferation, and apoptosis. Ubiquitin-proteasome pathway is well known in the prior art.

Intracellular proteolysis is the most recently discovered regulatory system of cellular physiology. Everything from cell division, development, and differentiation to cellular senescence has a proteolytic component. There is no simpler way to stop a physiological process than to destroy one of the components of a pathway in a controlled fashion. The discovery of the role of ubiquitin in the proteolytic pathway earned Aaron Ciechanover, Avram Hershko and Irwin Rose the 2004 Nobel Prize in Chemistry. Several books have become available that further reveal the importance of ubiquitins in human biology and human disease control, some of which are included herein for reference only: Ubiquitin and the Chemistry of Life, Mayer et al., John Wiley, 2005; Ubiquitin, Rechsteiner et al, Plenum Press, 1988; The Ubiquitin System, Schlesinger et al., Cold Spring Harbour Lab, 1988; Ubiquitins and the Biology of the Cell, Peters et al., Plenum Press, 2001; Self-Perpetuating Structural States in Biology, Disease, and Genetics (2002), Proceedings of the National Academy of Sciences.

A wide variety of neurodegenerative disorders are associated with the accumulation of ubiquitinylated proteins (if they are not further degraded by Proteasomes) in neuronal inclusions, and also with signs of inflammation. In these disorders, the ubiquitinylated protein aggregates, which will be seen as a foreign body by immune system, may themselves trigger the expression of inflammatory mediators, such as cyclooxygenase 2 (COX-2). Impairment of ubiquitin-proteasome pathway may contribute to this neurodegenerative and inflammatory processes. Products of COX-2, such as prostaglandin J2, can, in turn, increase the levels of ubiquitinylated proteins and also cause COX-2 up-regulation, creating a self-destructive feedback mechanism [Zongmin Li et al., International Journal of Biochemistry and Cell Biology, vol. 35, 547-552 (2003)].

The disruption of the Ubiquitin-proteasome pathway can result from damaging events, such as aging-induced decrease in proteasome function [Garrard et al., International Journal of Biochemistry and Cell Biology, vol. 34, 1461 (2002)], oxidative stress [Shringarpure et al., Free Radical Biology Medicine, vol. 32, 1084-1089 (2002)], and production of neurotoxic molecules from mutations. A dysfunctional ubiquitin-proteasome pathway may then cause proteins that are normally turned over by this pathway to aggregate and form inclusions. One of the mechanisms by which the abnormal accumulation of ubiquitinylated proteins may mediate neurodegradation is by triggering an inflammatory response. Inflammation is a natural defense against diverse insults, intended to remove damaging agents and to inhibit their detrimental effects. Treatment of neurons with proteasome inhibitors, oxidative stressors, or cyclopentenone prostaglandin J2 elicits accumulation of ubiquitinylated proteins and cytotoxicity in a concentration-dependent manner. These agents also increased the neuronal levels of COX-2 and prostaglandin E2. COX-2 is the pro-inflammatory and inducible form of cyclooxygenases, which are enzymes that catalyze the rate-limiting step in the biosynthesis of prostaglandins, prostacyclins, or thromboxane A2 from their precursor arachidonic acid. Cyclooxygenases are bifunctional hemoproteins that catalyze the cyclooxygenation of arachidonic acid to PGG2 followed by the hydroperoxidation of PGG2 to PGH2. Specific enzymes, such as reductases, isomerases, and synthases, then convert PGH2 to other PGs (prostaglandins) and thromboxane A2. Reactive oxygen species (ROS) produced during this biosynthetic pathway are known to contribute to tissue damage. The pro-oxidant effect of prostaglandin J2 could me mediated by its cyclopentenone ring that contains an alpha-beta-unsaturated carbonyl group that can react with sulfhydryl group of cysteine residues in glutathione and cellular proteins to inhibit ubiquitin isopeptidase activity. This may also contribute to the accumulation of ubiquitinylated proteins. This toxic positive feedback may create a self-destructive mechanism that contributes to the neurodegenerative process. Neurodegenerative disorders, such as Alzheimer's disease, Parkinson's disease, and amylotropic lateral sclerosis, found to be associated with the accumulation of ubiquitinylated proteins in neuronal inclusions also exhibit signs of inflammation. Ross et al. [Trends Cell Biol., vol. 14(12):703-11 (2004)] provide a detailed discussion of the ubiquitin-proteasome pathway in Parkinson's disease and other neurodegenerative diseases. Burger et al. [Eur. J. Cancer, vol. 40(15):2217-29 (2004)] provide an insight into the ubiquitin-mediated protein degradation pathway in cancer therapeutic implications. A book edited by Peters et al, "Ubiquitin and the Biology of the Cell", Plenum Publishing, provides information on the importance of ubiquitin in modulating cellular functions.

The modulation of ubiquitin-proteasome pathway can be achieved in several manners that includes, (1) the inhibition of thioester bond formation between ubiquitin and cysteine moiety of ubiquitin activating enzyme (E1, E2, or E3), (2) the inhibition of iso-peptide bond formation between ubiquitin and lysine moiety of target protein (3) the inhibition of ubiquitin-proteasome complex, (4) acceleration of proteolysis by ubiquitin-proteasome complex (acceleration of proteasome ligase, E3, action), (5) selective inhibition of cyclooxygenase enzyme, (6) use of thiol reducing antioxidants, (7) caspase inhibitors, and (8) use of molecular chaperones to attenuate the accumulation of ubiquitinylated proteins. The molecular chaperones could thus be highly beneficial in the reduction of inflammation caused by accumulating ubiquitin-proteasome complex, which could be useful for the treatment of skin aging, inflammation, ulcer and wound healing, and enzyme malfunction related ailments, and this aspect is the focal point of the present invention.

Ubiquitin contains 76 amino acids (one letter code: MQIFVKTLTGKTITLEVEPSDTIEN-VKAKIQDKEGIPPDQQRLIFAGKQ LEDGRTLSDY-NIQKESTLHLVLRLRGG), of which gly-gly dipeptide is at the carboxy-terminal. It is believed that the compounds of the present invention block the above gly-gly binding site, thus acting as molecular chaperones to attenuate the accumulation of ubiquitinylated proteins.

Acne, Rosacea, and Facial Oil Control Benefits.

Acne is caused by a combination of several factors. In a previous disclosure (U.S. patent application Ser. No. 10/248, 691; filed Feb. 10, 2003; now abandoned) the present inventor has discussed that acne is a group of diseases whose initial pathology is the comedo and includes acne vulgaris, neonatal acne, infantile acne, and pomade acne. There are approximately 45 million people who suffer from acne in America alone. The disease is so common in youth at their puberty that it often has been termed physiological. Although acne stops appearing for most people by the age of 25, some people, the majority of them are women, experience the disease well into their adult life. This "adult acne" differs from teenage acne in location and that it tends to be more inflammatory with fewer comedones. As the human concern for facial beauty continues to receive heightened marketing attention, the cure for various forms of acne has received much attention, as evidenced by the number of patents and patent applications that have appeared recently. The patent literature abounds with acne treatments. From January 2001 to January 2003 time period over 900 patent applications were published in U.S. patent applications computer database search that related to acne. From 1975 to January 2003, there were over 9000 patents issued by the U.S. Patents Office that had some reference to acne. From these data, it would become obvious that a suitable solution to this problem has eluded past efforts.

The disease of acne is characterized by a great variety of clinical lesions. Although one type of lesion may be predominant (typically the comedo), close observation usually reveals the presence of several types of lesions (comedones, pustules, papules, and/or nodules). The lesions can be either non-inflammatory or, more typically, inflammatory. In addition to lesions, patients may have, as the result of lesions, scars of varying size. The fully developed, open comedo (i.e., a plug of dried sebum in a skin pore) is not usually the site of inflammatory changes, unless the patient traumatizes it. The developing microcomedo and the closed comedo are the major sites for the development of inflammatory lesions. Because the skin is always trying to repair itself, sheaths of cells will grow out from the epidermis (forming appendageal structures) in an attempt to encapsulate the inflammatory reaction. This encapsulation is often incomplete and further rupture of the lesion typically occurs, leading to multi-channeled tracts as can be seen in many acne scars.

In general, there are four major principles presently governing the therapy of acne: (i) correction of the altered pattern of follicular keratinization; (ii) decrease sebaceous gland activity; (iii) decrease the follicular bacterial population (especially *P. acnes*) and inhibit the production of extra cellular inflammatory products through the inhibition of these microorganisms, and (iv) produce an anti-inflammatory effect. Acne is a chronic inflammatory disease affecting the sebaceous glands. Acne lesions primarily involve the sebaceous glands located on the face, neck, chest and back. Both closed comedones (blackheads) and open comedones (whiteheads) are caused by hyperkeratinization of the infundibulum of the sebaceous duct. These keratinous plugs block the flow of sebum. These dilated ducts abound with the colonies of *Propionibacterium acnes* and other fat splitting organisms. The clinically evident open and closed comedones and the microscopic microcomedo are the signal lesions of acne. The acne process results from a cascade of events. First, at puberty a spike in androgen production heralds an increase in sebum production and begins the hyperkeratinization process causing microcomedones and sebum blockade. With this blockage, the number of resident follicular flora increases dramatically. These bacteria produce inflammatory products, which permeate through thin walls of dilated sebum-filled duct. Once in the perifollicular dermis, they trigger the body's own immune defenses (both acute and granulaomatous) to produce the characteristic inflammatory papules, pustules and nodules characteristic of inflammatory acne. The term "acne" is used herein as a general term to include inflammatory diseases of the pilosebaceous unit. In the medical field, the specific type of acne is usually indicated by a modifying term, although the term acne is frequently used alone to designate common acne or acne vulgaris.

Thus, there are four factors that are believed to be the contributors of acne: (1) Increased sebum production; (2) Comedo formation, in which the follicular infundibulum hypercornifies, hyperkeratinizes, and hypodesquamates; (3) Colonization of the follicule by anaerobic *Propionibacterium*, mainly *P. acnes*; and (4) The host's inflammatory response. The above four factors are interrelated to each other. Sebum is comedogenic and causes inflammation by itself. *Propionibacterium acnes* is a relatively slow growing, (typically) obligate anaerobe gram-positive bacterium that is linked to the skin condition acne. An anaerobic organism or anaerobe is any organism that does not require oxygen for growth. Obligate anaerobes will die when exposed to atmospheric levels of oxygen.

The *Propionibacterium* has high lipolytic activity and liberates free fatty acids from sebum lipids. The free fatty acids have been shown to cause marked inflammation. The microorganisms also produce other extracellular enzymes such as proteases and hyaluronidases, and chemotactic factors, which may be important in the inflammatory process. It would thus be advantageous to provide relief from all of the above four principal causes of acne.

Rosacea is a common facial dermatitis that currently affects an estimated 13 million Americans. It is a chronic and progressive cutaneous vascular disorder, primarily involving the malar and nasal areas of the face. Rosacea is characterized by flushing, erythema, papules, pustules, telangiectasia, facial edema, ocular lesions, and, in its most advanced and severe form, hyperplasia of tissue and sebaceous glands leading to rhinophyma. Rhinophyma, a florid overgrowth of the tip of the nose with hypervascularity and modularity, is an unusual progression of rosacea of unknown cause. Ocular lesions are common, including mild conjunctivitis, burning, and grittiness. Blepharitis, the most common ocular manifestation, is a nonulcerative condition of the lid margins. Rosacea most commonly occurs between the ages of 30 to 60, and may be seen in women experiencing hormonal changes associated with menopause. Women are more frequently affected than men; the most severe cases, however, are seen in men. Fair complexioned individuals of Northern European descent are most likely to be at risk for rosacea; most appear to be pre-disposed to flushing and blushing.

The cause of rosacea is poorly understood, numerous theories have been offered. Hypotheses have included gastrointestinal, psychological, infectious, climatic, and immunological causes, although scientific evidence has not substantiated any of these as primary. Controlled studies have not demonstrated consistent preponderance of gastrointestinal symptoms in rosacea patients. Similarly, neither a distinct psychological abnormality nor one pharmacological mechanism has been isolated in rosacea patients. Perhaps the most commonly touted of the etiologic theories is based on the presence of Demodex folliculorum mites in patients with rosacea; the organism feeds on sebum, and in some cases treatment of demodex infestation has noted improvement in the rosacea; however, in a review of 79 biopsies in 1969, Demodex folliculorum was noted in only 19% of the specimens. A bacterial cause for the disease has been hypothesized, but no consistent findings of one bacterium have been demonstrated. Climate, specifically exposure to extremes of sun and cold, may have an effect on the course of the disease, but the role of climate in what appears to be a connective tissue disorder is not clear.

An autoimmune process has been suggested, and tissue-fixed immunoglobulins have been reported in patients with chronic inflammation of rosacea, but no other evidence has been found. Other experimental evidence has suggested this disease may represent a type of hypersensitivity reaction. No single hypothesis appears to adequately explain both the vascular changes and the inflammatory reaction seen in rosacea, leaving the pathogenesis unclear. More recently, certain investigators have suggested a connection between rosacea and *H. pylori*, bacteria shown to cause certain gastrointestinal ulcers, because symptoms seem to have abated in some ulcer patients also suffering rosacea. Nevertheless, the connection between *H. pylori* and rosacea has been questioned. H. Herr, J. Korean Med Sci Oct. 15, 2000; (5):551-4; R. Boni, Schweiz Med Wochenschr Sep. 16, 2000; 130(37): 1305-8).

Kang et al. (U.S. Patent Application 20020183399) have recently concluded that rosacea and acne have many common features in their onset and cure. The topical composition for treating rosacea, which comprises a combination of an anti-microbial and at least one of (a) an anti-inflammatory and (b) a non-retinoid inhibitor, are very similar for treating acne, according to Kang, for example. It would thus appear logical to develop broad-spectrum compositions that can treat both acne and rosacea, although such compositions are still unknown, until now.

Most acne treatments are directed at preventing inflammatory lesions, particularly the larger nodulo-cystic lesions that tend to be destructive and lead to permanent scarring. In general, visible comedones are the only minor cosmetic nuisances and do not lead to inflammatory lesions. Most acne treatment is directed to four areas: (1) Keratinous plugs in sebaceous ducts; (2) Large sebaceous glands producing excess sebum; (3) Increased numbers of resident follicular bacteria; and (4) Inflammatory response to chemical mediators passing through the follicular wall.

Topical products used to remove comedones are known as comedolytics, the most effective being tretinoin, marketed as a prescription product (Retin A) and by several generic companies. Tretinoin or all-trans retinoic acid is the naturally occurring metabolite of Vitamin A. Tretinoin increases epidermal cell turnover, thus causing comedolysis and most importantly prevents the formation of new keratinous plugs. Applications of tretinoin are normally once a day at bedtime. Dryness, stinging and redness sometimes accompany the applications. Importantly, improvement is usually not seen for 6-8 weeks. Adapalene 0.1% (Differin) is a topical retinoid like tretinoin. Available by prescription only, the gel is usually applied once nightly. Side effects include frequent scaling, burning, redness and dryness. Improvement is delayed and is not evident for 4-8 weeks. Sodium sulfacetamide 10%/sulfur 5% (Sulfacet-R) is also available by prescription only. It is a lotion with antibacterial and comedolytic action. As with tretinoin, improvement is seen in 4-8 weeks. Salicylic acid 2% is an over the counter product that exhibits mild comedolytic activity.

The only products that have anti-sebum activity are estrogens and 13 cis-retinoic acid (isotretinoin) and these must be used systemically to be effective. Isotretinoin (Accutane) is a metabolite of Vitamin A available by prescription only. Isotretinoin is used to treat only severe cystic or conglobate acne. Because of its teratogenic properties, birth defects can occur. Isotretinoin is a powerful drug and can elevate triglycerides, total cholesterol and decrease high-density lipoproteins (HDL). Other side effects include dry skin, dry eyes, itching, headaches, nosebleed, and photosensitivity. It is generally taken for 4-5 months to see improvement. Recently, one brand of oral contraceptive has been approved for the treatment of acne for patients who request birth control.

A number of topical and systemic agents are used to lower the number of bacteria that colonize the follicular duct. These include benzoyl peroxide (BP), BP 5%/erythromycin 3% (Benzamycin). BP has antibacterial activity and drying effects and is available over the counter or by prescription. Moreover, it has been recently reported that benzoyl peroxide seems to induce free radical production that can produce skin changes that qualitatively resemble ultraviolet B damage, e.g., increases in epidermal thickness, and deleterious changes in elastin and glycosaminoglycans content (Ibbotson, S. H., et al., J. Inves. Derm., 1999, 112: 933-938). In addition, Benzoyl peroxide is highly reactive, and is thus difficult to stabilize in practical compositions. BP is applied once or twice daily for 1-2 months. BP can produce erythema and peeling of skin. BP is often tried first for both non-inflammatory and mild inflammatory acne. Other topical antibiotics include clindamycin and erythromycin. These are used as solutions, lotions or gels by prescription only. Usually they are applied once or twice daily and results are seen in 1-2 months. Azelaic acid 20% (Azelex) also has mild antibacterial effects. Systemic antibiotics include tetracycline and its analogs, which are used in low doses for years or until the end of the acne prone years. Most patients with mild inflammatory acne receive a combination of topical antibiotics and tretinoin or other retinoid. Bacterial resistance does occur so antibiotics may be changed or BP is substituted since resistance does not occur with BP. More severe acne requires systemic antibiotics and topical retinoid. The most severe must receive oral isotretinoin for 4-5 months.

There are no drugs that directly affect the inflammatory acne. The retinoids do have some anti-inflammatory properties, but these are poorly described. Topical steroid and even systemic steroids have been used to abort a severe flare of fulminant acne, but these are limited uses because of the side effects. Benzoyl peroxide gels are sometimes used as first aid on acne lesions. These function as a "drawing poultice", but data supporting this use is not available.

The treatment for acne centers on opening the pore, killing *P. acnes*, reducing sebum production and regulating inflammatory responses. Retinoids are the agents to reduce sebum production and open the pore. As a topical agent, Differin (adapalene) or Retin-A (tretinoin) is used for mild and moderate acne. Isotretinoin, an oral drug, is very effective but reserved for the severe and resistant acne because of its teratogenicity, hepatotoxicity, elevating triglyceride level and other side effects.

For topical applications, the Food & Drug Administration (FDA) has approved the following ingredients for marketing topical acne products in the USA (Code of Federal Regulations, 21CFR333.310); (1) Resorcinol (2%, in combination only); (2) Resorcinol monoacetate (3%, in combination only); (3) Salicylic acid 0.5 to 2 percent, and (4) Sulfur 3 to 10 percent.

Salicylic acid has been used to treat acne for some time. Salicylic acid dries the skin, which helps in acne management, but it also causes skin irritation in perilesional skin areas of acne patients, especially patients with sensitive skin, and in some cases the erythema is extreme. Salicylic acid is also pH-sensitive, as in neutralized forms, such as sodium salicylate or triethanolamine salicylate; there is a loss of efficacy due to poor bioavailability. In free acid form, salicylic acid is absorbed rapidly and transported into bloodstream. This is the reason for its irritation-causing problems. It would thus be advantageous if salicylic acid can be provided in a form that is slow to absorb into deeper layers of skin for its maximum topical bioavailability and anti-acne efficacy.

Topical and oral antibiotics, especially tetracycline, erythromycin, and clindamycin, are sometimes prescribed for patients with inflammatory papules and pustules. However, in addition to the undesirability of antibiotic overuse in general, which can lead to enhance susceptibility to infection, disadvantages to such treatments include phototoxicity and interactions with other medications. Other factors that play a role in exacerbating acne, including oil-based cosmetics and some drugs (e.g., androgenic hormones, high-progestin birth control pills, systemic corticosteroids, and iodide- and bromide-containing agents) are often minimized during acne treatment. Besides the side effects of the antimicrobial agents, development of resistant microorganisms has become an important issue nowadays. The number of patients harboring resistant P. acnes has been shown to be growing. For this reason, it would be advantageous to exclude antibiotics and antibacterial agents from topical preparations for acne.

For efficacious topical treatments, it would thus be advantageous to include the following six-prong provisions to control fundamental elements that can provide control of both acne and rosacea in a single composition: (1) Control of excess sebum production; (2) Control of undesirable bacteria and mites; (3) Control of inflammation; (4) Enhanced desquamation of follicular infundibulum cells; (5) Reduction of irritation from anti-acne and anti-rosacea compositions themselves; and (6) An enhancement of the topical bioavailability of anti-acne and anti-rosacea compositions.

Since the resistance to bacteria is becoming a problem, it would be advantageous to control bacteria without using an antibacterial agent. Also, salicylic acid is being one of the most favored and inexpensive ingredients to control acne, albeit its irritation causing side effects, it would be advantageous to devise methodologies to increase both topical bioavailability and anti-acne efficacy of salicylic acid with a reduction in its irritation causing side effects.

The prior art literature abounds with acne and rosacea treatments. From January 2001 to January 2003 time period over 900 patent applications were listed in U.S. patent applications computer database search that related to acne. From 1975 to January 2003, there were over 9000 patents issued by the U.S. Patents Office that had some reference to acne. In the same period, there were over 400 patents that had a reference to rosacea. It may also be appreciated that the study and treatment of rosacea has been a long-time concern of the medical community. For example, about 1,000 medical papers have been published on this subject. From these data, it would become obvious that a suitable solution to acne and rosacea problems has not yet been found. A discussion of the patents and patent applications most pertinent to the present invention follows. U.S. Patent Application 20030021855 (Perricone) discloses acne prevention by the topical application of compositions containing an alkanolamine such as dimethylaminoethanol, in combination with tyrosine and a sulfur ingredient such as lipoic acid or glutathione. Such alkanolamines have strong amine odor that is objectionable to consumers for application on face. Moreover, several such alkanolamines have a high pH that can cause irritation. U.S. Patent Application 20030021816 (Kang) discloses an immunosuppressant compound, a second active ingredient selected from the group consisting of comedolytics, antibacterials, anti-inflammatory, retinoids, glucocorticoids, and mixtures thereof, and a dermatologically acceptable carrier for acne treatment. Such immunosuppressants are not readily available for common use. U.S. Patent Application 20020192298 (Burrell) relates to the use of antimicrobial metals, preferably silver for the treatment of acne. It is preferred that the use of any antimicrobial agents for acne treatment be minimized or eliminated due to development of resistant bacteria. U.S. Patent Application 20020172672 (Sieberg) is directed to the use of serine proteases, either alone or in combination with a retinoid compound in a pharmaceutical or cosmetic composition for acne treatment. Such enzyme preparations can cause serious skin allergy in some humans. U.S. Patent Application 20020155180 (Goodman) discloses treatment of acne that comprises topically applying an effective amount of a saw palmetto berry extract and one or more constituents that enhance penetration of the extract into hair follicle sebaceous glands. This disclosure is specific to one ingredient, hence of limited application. U.S. Patent Application 20020151527 (Wiegand) discloses a method for reducing the number and severity of acne lesions comprising administering a sensory regimen to down regulate the activity of the hypothalamus-pituitary-adrenal axis, in combination with the administration of a topical anti-acne composition comprising an anti-acne agent selected from salicylic acid, sulfur, lactic acid, glycolic acid, pyruvic acid, urea, resorcinol, N-acetylcysteine, retinoic acid, benzoyl peroxide, octopirox, triclosan, azelaic acid, phenoxyethanol, phenoxypropanol, flavinoids, derivatives thereof, and mixtures thereof. The problems of salicylic acid irritation and low topical bioavailability and the use of antibacterials are still not eliminated by Wiegand. U.S. Patent Application 20010056071 (Pelicchia) discloses the application of antioxidant resveratrol for acne treatment. U.S. Pat. No. 6,451,773 (Oester et al.) discloses a combination of chitosan with azelaic acid, benzoyl peroxide, retinoic acid, salicylic acid, or mixtures thereof, for the treatment of acne. Chitosan is used as a film-forming agent for topical application of other active ingredients for better adhesion to skin surface. While topical bioavailability is enhanced, the skin irritation and other problems of salicylic acid and azelaic acid use are not reduced. U.S. Pat. No. 6,440,994 (Sanders) discloses acne treatment using a mixture of antihistamines and anti-inflammatory agents. This does not provide a multifaceted treatment objective. U.S. Pat. No. 6,436,417 (Singh) discloses solubilized forms of salicylic acid for acne treatment. Such solubilized forms absorb more quickly, reaching bloodstream at a faster rate. Both the topical anti-acne efficacy may be lower and skin irritation may be higher for such compositions. U.S. Pat. No. 6,433,024 (Popp et al.) discloses topical anti-acne compositions based on benzoyl peroxide, an alpha hydroxy acid, a moisturizer, an isosorbide and a detergent. These compositions contain several skin irritating ingredients. U.S. Pat. No. 6,365,623 (Perricone) discloses one preferred embodiment that contains a combination of lipoic acid, an alpha-hydroxy acid, and dimethylaminoalcohol. Lipoic acid is also claimed to cure rosacea (U.S. Pat. No. 6,472,432; Perricone). U.S. Pat. No. 6,262,117 (Sefton) discloses acne treatment based on a combination of benzoyl peroxide and azelaic acid. The poor stability of benzoyl peroxide and the skin irritation of either benzoyl peroxide or azelaic acid are still unsolved in Sefton disclosure. U.S. Pat. No. 6,168,798 (O'Halloran et al.) discloses an alcoholic solution of salicylic acid and salicylates for acne treatment. The rapid absorption of such clear solutions into skin would reduce the topical bioavailability of the active ingredients in such compositions. U.S. Pat. No. 5,989,523 (Fitzjarrell et al.) discloses a topical spray comprising niacinamide, Aloe Vera extract and NaPCA in a water carrier base. U.S. Pat. No. 5,910,312 (Fried) discloses an anti-acne composition comprising benzoyl peroxide, salicylic acid, and a vasoconstrictor in an inert carrier. Benzoyl peroxide has been suggested for treating acne vulgaris. (See U.S. Pat. No. 4,387,107.) For many years, benzoyl peroxide has been proven to be a particularly powerful keratolytic and anti-seborrhic agent, as well as being endowed with antibacterial properties. Topical benzoyl peroxide compositions, including a vehicle to enhance the efficacy thereof, are known (See U.S. Pat. No. 4,411,893). Topical compositions of benzoyl peroxide combination with antibiotics are also known. (See U.S. Pat. Nos. 4,407,794; 4,692,329 and 4,387,107). The problems of skin irritation from benzoyl peroxide or salicylic acid, and the chemical instability and reactivity of benzoyl peroxide are still not solved; complex, dual-chamber delivery systems (such as U.S. Pat. Nos. 6,462,025 and 6,448,233) have been disclosed.

Rosacea is, while rare among colored races, common among races with a light-colored skin, especially among white races, and many cases occur among them. It is divided according to the symptoms into the first degree (telangiectatic rosacea on the forehead, cheeks, dorsum nasi), the second degree (acne rosacea, coexistence of follicular papules and pustules), and the third degree (rhinophyma, dark red tumor and dilated pore on apex nasi). It starts with facial flush (redness) and eventually involves serious impairment of appearance, developing papules, pustules, rhinophyma and tumor on apex nasi, it is also accompanied by seborrhea or enhancement of feeling of heat on the face due to emotional stress or change of environmental temperature. Thus, these symptoms give a patient mental and physical suffering. For the time being, the real cause of rosacea is unknown (Hifuka Chirya Handbook, pp. 380-381, Nanzando (1987) and Gerd Plewing, Albert M. Kligman, ACNE and ROSACEA, 2nd, Completely Revised and Enlarged Edition, pp. 431-454, Springer-Verlag (1993)). Rosacea is apt to be confused with acne. Rosacea, which can coexist with acne, essentially differs from acne. It is characterized by facial flush due to vascularization and proceeds with acne rosacea and tumor on apex nasi. The etiology of rosacea is not fully known, however, at least four factors or co-factors have been suggested. The first of these is endocrine in that the disease occurs most frequently in women between the ages of thirty and fifty. As such, one definite type of rosacea is believed to have a hormonal basis. A second factor is vasomotor liability, believed to have some connection with menopause, which brings about an impairment of normal or consistent flow of blood to the face and its capillaries. Therein, excessive flow of blood to the face, i.e., the well-known "hot flashes" of menopause, is believed to constitute a factor in the disease and its pathogenesis. More particularly, it has been proven that increased skin temperature, as occurs in facial flushing, increases susceptibility to the condition. Rosacea has also been observed as a side effect or immune response to the use of certain cortisone products, which can bring about a severe form of the condition. Finally, pathology analysis of the expressed contents of inflamed pustule follicle of the nose in acute rosacea has demonstrated the existence of demodices, which is a signature of the ectoparasite demodex folliculorum. Accordingly, in such cases, a specific external pathogenic factor is evident. This factor is not present in other forms of acne, e.g., acne vulgaris.

However, the information available so far does establish that both acne and rosacea are interrelated, and hence a common treatment for both would be highly desirable.

Relative to rosacea treatment compositions, U.S. Pat. Nos. 6,352,724 and 5,654,013 (Taylor et al.) discloses rubbing common salt (Sodium chloride). Sodium chloride is the subject of additional disclosures for the treatment of both acne and rosacea (U.S. Pat. No. 4,443,442 to Skillern; U.S. Pat. No. 3,867,522 to Kligman). However, such treatments only work by a single biochemical mechanism, that of abrasion and debridement of the affected skin. Also, once the debridement is completed, the affected skin will feel pain, since it will be equivalent to "adding salt to injury". U.S. Pat. No. 6,174,534 (Richard et al.) provides a composition that contains long chain fatty acids for rosacea treatment. Although such composition may be suitable for rosacea, such fatty acids may actually exacerbate acne due to excess sebum-like activity from such fatty acids. U.S. Pat. No. 6,136,806 (Hittel) discloses certain synthetic organic molecules for rosacea treatment that are not commonly available, or available by prescription only in certain countries. U.S. Pat. No. 6,133,310 (Parks) and U.S. Pat. No. 5,952,372 (McDaniel) disclose the application of Invermectin in the treatment of rosacea. This ingredient has also been used frequently for the treatment of acne. Invermectin, however, provides relief by a single biochemical mechanism, not a six-prong approach. Moreover, Invermectin is not commonly available. U.S. Pat. No. 5,972,993 (Ptchelintsev) discloses the application of certain antioxidants for the treatment of rosacea. This treatment is thus based only on a single approach of anti-inflammatory action of such antioxidants. U.S. Pat. No. 5,667,790 (Sellers) discloses the application of aluminum salts for acne and rosacea treatment. Such aluminum salts only block the exudation of sebum and provide relief probably by astringent action. Their long-term use can actually cause additional inflammatory response. U.S. Pat. No. 5,885,595 (Corey) discloses esters of retinal for acne and rosacea treatment. U.S. Patent Application 20020013361 (Perricone) claims the use of lipoic acid. Since lipoic acid is an antioxidant, it probably works by anti-inflammatory biochemical mechanism, thus constituting just one-prong treatment. U.S. patent applications 20020172719, 20020054918, and 20020041901 (Murad) disclose pharmaceutical composition and methods for the cleansing of skin to facilitate the prevention, treatment, and management of skin conditions that include rosacea and acne by a composition that includes a hydroxy acid or tannic acid to exfoliate a portion of the skin, stabilized hydrogen peroxide to facilitate cleansing of the skin, and an antimicrobial agent to inhibit or reduce microorganisms on the skin. Since the overuse of antimicrobial agents can cause further problems, as mentioned earlier, Murad inventions are thus of limited application, or even to be possibly avoided for any long-term rosacea and acne treatment regimen.

It is thus both surprising and unexpected that the compositions of the present invention relieve the symptoms of acne and also rosacea. The exact mechanism of this action is not well understood at this time. However, this does not reduce the significance or utility of the present invention for consumer applications.

Mazzio et al (U.S. patent application Ser. No. 2004185123) disclose a topical herbal formulation for preventing and/or treating dyshidrosis (pompholyx), non-responsive to topical steroids. The formulation may also be used to treat contact dermatitis, eczema, palmoplantar pustulosis and skin infections incurred by invasive pathogens such as mold, fungus and bacteria. The formulation is comprised of plant extracts and niacin, that when combined yield an effective multifaceted pharmaceutical approach to treating dry skin disorders. The active ingredients within the formula include a combination of dry, aqueous, acid and alcohol extracts of black walnut hull (*Ouglans Nigra*), wormwood (*Artemisia Absinthium*), tumeric rhizome (*Curcuma Longa*), garlic (*Allium sativum*), chamomile (*Matricaria Chamomile*), licorice root (*Glycyrrhiza Glabra*), St. Johns wort (*Hypericum perforatum*), aloe vera, niacin and herbal anti-bacterial agents.

The present inventor hypothesizes possible mechanism(s) for anti-acne activity of the present invention. Acne is caused, among other factors, by *Propionibacterium acnes*. Most bacteria are greatly dependent on iron (in Fe3+ state) for their metabolic activity. This Fe demand is greater that Fe requirements of normal human cells. The bacterial iron transport has been extensively studies in the prior art, for example Nielands et al. [Adv. Inotg. Biochem., 5, 137 (1983); Struct. Bonding (Berlin), 58, 1 (1984)]. The agents responsible for iron transport into and within bacteria have been extensively studied, and many structural and chemical details have been firmly established. The problem is that iron is not spontaneously available to oxic (aerobic) organisms in an aqueous environment because of the very low solubility of ferric hydroxide (pK about 38). Thus Fe3+ ions at a pH of about 7 have a molar concentration of only about 10(−18), and simple diffusion into cells could never suffice to supply their needs. Indeed, simple inward diffusion would not occur, since iron is already more concentrated than this in the living cell. Therefore special chelating agents called "siderophores" are produced by bacteria and ejected into their environment to gather iron and transport it through the cell wall into the cell. In some cases it appears that the chelator at the cell wall releases iron and it passes through alone, whereas in others the entire complex enters the cell.

The siderophores are rather diverse chemically but have in common the use of chelating, oxygen-donor type ligands. A very large number of siderophores that have been characterized employ hydroxamate moieties, —CO—N—O(−), as the ligands. The structure of a siderophore, called a "ferrichrome" consists of a cyclic hexapeptide in which three successive amino acid residues have side chains ending in hydroxamate groups.

Another type of siderophore, especially common in prokaryotes such as enteric bacteria is called an "enterobactin"; the ligating units are catecholate anions that also chelate very effectively [Raymond et al., J. Am. Chem. Soc., 107, 6920 (1985)].

Iron-Sulfur proteins are relatively low molecular weight compounds consisting of peptide chains bound though cysteine sulfur atoms to redox centers that consist either of one iron atom or a cluster of iron and sulfur atoms, the latter often being called "inorganic" sulfur atoms to distinguish them from the sulfur atoms of the cysteine residues. The term "rubredoxin" is used for those with one iron atom, while those containing clusters are called "ferredoxins".

Rubredoxins are found in anoxic (anaerobic) bacteria where they are believed to participate in biological redox reactions. They are relatively low molecular weight proteins (about 6000 amu) containing only one iron atom. In the best-characterized rubredoxin, from the bacterium *Clostridium pasturianum*, the iron atom, which is normally in the III oxidation state, is surrounded by a distorted tetrahedron of cysteinyl sulfur atoms. The Fe—S distances range from 2.24 to 2.33 Angstroms (A), and the S—Fe—S angles from 104 to 114 degrees. When the Fe (III) is reduced to Fe (II) there is a slight (0.05 A) increase in the Fe—S distances. However, Mossbauer spectroscopy shows that Fe is actually present both in (III) and (II) oxidation states. Ferredoxins are also relatively small proteins (about 6000-12000 amu) in which the redox centers, clusters of two, three, or four iron atoms, each with an equal number of sulfur atoms are held in place by bonds from cysteine sulfur atoms to iron.

From the above discussion it can be seen that a distortion of rubredoxin, ferredoxin, ferrichrome siderophore, and enterobactin siderophore can cause a disruption of bacterial metabolism. Thus, the bacteria may not be killed via the antibacterial action, but their multiplication by cell division may be hampered for their further growth.

In an unexpected and surprising discovery it has now been found that the compositions of the present invention bind with rubredoxin moiety of *Prionionibacterium* acnes. When this bound form of rubredoxin enters the acne bacterium the cellular redox functions are inhibited. This causes the acne bacterium to cease its metabolic activity. However, this is only one mechanism for anti acne activity of the present invention. There are several other possible modes of anti-acne action, as mentioned above, which are yet unknown for the benefits rendered by the present invention. As stated before, this should not preclude the utility of this invention.

Control of Dark Spots. Inhibition of phenylalanine hydroxylase and Phenylalanine Transaminase.

The biosynthetic pathways from shikimic acid leading to the formation of melanin are summarized in FIG. 1 that will be used as a reference for subsequent discussions.

FIG. 1.

Phenylalanine hydroxylase is responsible for the first step in the conversion of phenylalanine into tyrosine. Tyrosine is required for the production of melanin, which gives color to hair and skin. Phenylalanine hydroxylase must work in combination with tetrahydrobiopterin to perform this function. Phenylalanine hydroxylase contains iron in its active site, and tetrahydrobiopterin is required in proximity to this active site.

It is both surprising and unexpected that compositions of the present invention inhibit phenylalanine hydroxylase. Although the mechanism of this inhibition is not fully clear at this time, it is theorized that the binding of iron metal at the active site of Phenylalanine hydroxylase (Reaction Step 8, FIG. 6) and/or binding with Fe at tetrahydrobiopterin could be the cause for this effect.

Control of Dark Spots. Inhibition of tyrosine transaminase and Monophenol Monooxygenase (Tyrosinase).

Tyrosinase [EC:1.14.18.1] is a complex group of copper monooxygenases that catalyses the hydroxylation of monophenols and the oxidation of ortho-diphenols to ortho-quinones. This enzyme, found in prokaryotes and eukaryotes, is involved in the formation of pigments such as melanins and other polyphenolic compounds. Tyrosinase binds two copper ions (CuA and CuB). It has been shown that three conserved histidine residues bind each of the two copper ions. The regions around these copper-binding ligands are well conserved and also shared by some hemocyanins, which are copper-containing oxugen carriers from the hemolymph of many mollusks and arthropods. At least two peoteins related to tyrosinase are known to exist in mammals, and include TRP-1, which is responsible for the conversion of 5,6-dihydroxyindole-2-carboxylic acid (DHICA) to indole-5,6-quinone-2-carboxylic acid; and TRP-2, which is the melanogenic enzyme DOPAchrome tautomerase [EC:5.3.3.12] that catalyzes the conversion of DOPAchrome to DHICA. TRP-2 differs from tyrosinases and TRP-1 in that it binds two zinc ions instead of copper.

The inhibition of melanin synthesis can thus be achieved via several pathways, including the inhibition of tyrosine transaminase (inhibition of amination of hydroxyphenyl Pyruvate or phenyl Pyruvate (Step [7] and/or [4], FIG. 1), which leads to eventual inhibition of tyrosine biosynthesis. The melanin synthesis can also be blocked by the inhibition of monophenyl monooxygenase (EC 1.14.18.1), which converts tyrosine into dopaquinone via the intermediacy of dopa. In a surprising and unexpected discovery, the compositions of the present invention inhibit both tyrosine transaminase and monophenyl monooxygenase. The precise mechanism of this inhibition is not known at this time, but it is hypothesized that the compositions of the present invention bind with Fe in the active-site of monophenyl monooxygenase. Regardless of the actual biochemical mechanism the importance of this invention remains unexpected and novel.

Skin Brightening and Antiwrinkle-Antiaging Applications.

The compositions of the present invention provide an unexpected inhibition of MMP, tyrosinase, and tyrosine biosynthesis enzymes. The down-regulation of MMP leads to reduced degradation of connective issue such as collagen and fibrin. This results in increased suppleness of skin, leading to reduced visible skin wrinkles from aging. The decreased biosynthesis of tyrosine and dopa, and inhibition of Tyrosinase and tyrosine precursor enzymes leads to skin brightening effects, all of which are both surprising and unexpected when taken as a group of such desirable benefits. In normal practice, such group of desirable benefits is usually achievable only from a combination of several ingredients. The compounds providing good skin brightening are of formula (VII), and isomers and salts thereof.

Wound Healing Applications.

The compositions of the present invention provide an unexpected wound healing benefit with little scar tissue formation or skin pigment discoloration.

The entire wound healing process is a complex series of events that begins at the moment of injury and can continue for months to years. This overview will help in identifying the various stages of wound healing. I. Inflammatory Phase. A) Immediate to 2-5 days; B) Hemostasis, (i) Vasoconstriction, (ii) Platelet aggregation, and (iii) Thromboplastin makes clot; C) Inflammation, (i) Vasodilation, (ii) Phagocytosis. II. Proliferative Phase. A) 2 days to 3 weeks; B) Granulation, (i) Fibroblasts lay bed of collagen, (ii) Fills defect and produces new capillaries; C) Contraction, (i) Wound edges pull together to reduce defect; D) Epithelialization, (i) Crosses moist surface, (ii) Cell travel about 3 cm from point of origin in all directions. III. Remodeling Phase. A) 3 weeks to 2 years; B) New collagen forms which increases tensile strength to wounds; C) Scar tissue is only 80 percent as strong as original tissue.

Wound healing, or wound repair, is the body's natural process of regenerating dermal and epidermal tissue. When an individual is wounded, a set of events takes place in a predictable fashion to repair the damage. These events overlap in time and must be artificially categorized into separate steps: the inflammatory, proliferative, and maturation phases. In the inflammatory phase, bacteria and debris are phagocytized and removed and factors are released that cause the migration and division of cells involved in the proliferative phase. The proliferative phase is characterized by angiogenesis, collagen deposition, granulation tissue formation, epithelialization, and wound contraction. In angiogenesis, new blood vessels grow from endothelial cells. In fibroplasia and granulation tissue formation, fibroblasts grow and form a new, provisional extracellular matrix (ECM) by excreting collagen and fibronectin. In epithelialization, epithelial cells crawl across the wound bed to cover it. In contraction, the wound is made smaller by the action of myofibroblasts, which establish a grip on the wound edges and contract themselves using a mechanism similar to that in smooth muscle cells. As the cells' roles are close to complete, unneeded cells undergo apoptosis. In the maturation and remodeling phase, collagen is remodeled and realigned along tension lines and cells that are no longer needed are removed by apoptosis.

In the inflammatory phase, clotting takes place in order to obtain hemostasis, or stop blood loss, and various factors are released to attract cells that phagocytize debris, bacteria, and damaged tissue and release factors that initiate the proliferative phase of wound healing. When tissue is first wounded, blood comes in contact with collagen, triggering blood platelets to begin secreting inflammatory factors. Platelets also express glycoproteins on their cell membranes that allow them to stick to one another and to aggregate, forming a mass. Fibrin and fibronectin cross-link together and form a plug that traps proteins and particles and prevents further blood loss. This fibrin-fibronectin plug is also the main structural support for the wound until collagen is deposited. Migratory cells use this plug as a matrix to crawl across, and platelets adhere to it and secrete factors. The clot is eventually lysed and replaced with granulation tissue and then later with collagen. Platelets, the cells present in the highest numbers shortly after wounding, release a number of factors into the blood, including ECM proteins and cytokines, including growth factors. Growth factors stimulate cells to speed their rate of division. Platelets also release other proinflammatory factors like serotonin, brakykinin, prostaglandins, prostacyclin, thromboxane, and histamine, which serve a number of purposes, including to increase cell proliferation and migration to the area and to cause blood vessels to become dilated and porous.

Contrary to common belief, the use of any anti-inflammatory agents during the early stages of would-healing process is not desirable. On the same note, the over-expression of MMP-13 should be controlled from the onset of wound healing process to avoid apoptosis of newly formed connective tissue. Both connective tissue forming agents and anti-inflammatory agents are beneficial during the later stages of wound healing.

The exact mechanism of topical wound healing by the compositions of the present invention is believed to be due to the inhibition of Heme Oxidase, the exact nature if which is not yet known. However, this should not preclude the practical utility of the present invention in topical wound healing applications.

Treatment of Dandruff.

Recently, identification of *Malassezia* (formerly known as *Pityrosporum*, is a genus of related fungi, classified as yeasts; naturally found on the skin surfaces of many animals including humans) has been aided by the application of molecular or DNA based techniques. These investigations show that the *Malassezia* species causing most skin disease in humans, including the most common cause of dandruff and seborrhoeic dermatitis, is *M. globosa* (though *M. restricta* is also involved). The skin rash of tinea versicolor (pityriasis versicolor) is also due to infection by this fungus. So far, 10 species of *Malassezia* have been identified: *M. furfur, M. pachydermatis, M. globosa, M. restricta, M. slooffiae, M. sympodialis, M. nana, M. yamatoensis, M. dermatis,* and *M. obtuse.*

As the fungus requires fat to grow, it is most common in areas with many sebaceous glands: on the scalp, face, and upper part of the body. When the fungus grows too rapidly, the natural renewal of cells is disturbed and dandruff appears with itching (a similar process may also occur with other fungi or bacteria). The number of specimens of *M. globosa* on a human head can be up to ten million.

The compounds of the present invention have shown high activity against dandruff and seborrhea causing organisms.

The exact amount of each ingredient, or combinations thereof, to be used for various applications disclosed in the present invention is determined separately for each such application. In general, the amounts can vary from about 0.0001 percent by weight to about 50 percent by weight.

For the treatment of topical wounds, the inclusion of a Matrix metalloprotease (MMP) inhibitor is additionally beneficial. The said MMP can be selected, among others, from those disclosed by the present inventor in U.S. patent application Ser. No. 10/711,775, filed Oct. 4, 2004.

The compositions of the present invention can further include additional pharmaceutical or cosmetic active agent selected from a group of anti-acne agents comprising of salicylic acid, benzoyl peroxide, resorcinol, resorcinol monoacetate, sulfur, and combinations thereof.

The compositions of the present invention can further include additional pharmaceutical or cosmetic active agent for topical wound therapy, which can be selected, among others, from zinc ascorbate, copper Hyaluronate, zinc Hyaluronate, manganese Hyaluronate, copper Glucosamine complex, zinc Glucosamine complex, manganese Glucosamine complex, copper chondroitin, zinc chondroitin, manganese chondroitin, copper chondrosine, zinc chondrosine, manganese chondrosine, copper oleoresin complex, zinc aloeresin complex, manganese aloeresin complex, copper aloe emodin, zinc aloe emodin, and manganese aloe emodin.

The compositions of the present invention can be formulated in various cosmetic and pharmaceutical consumer products utilizing a variety of delivery systems and carrier bases. Such consumer product forms include the group consisting of shampoos, aftershaves, sunscreens, body and hand lotions, skin creams, liquid soaps, bar soaps, bath oil bars, shaving creams, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, conditioners, hair lighteners, coloring and non-coloring hair rinses, hair grooming aids, hair tonics, spritzes, styling waxes, band-aids, and balms.

In another preferred aspect, the delivery system or a carrier base are selected in the form of a lotion, cream, gel, spray, thin liquid, body splash, powder, compressed powder, tooth paste, tooth powder, mouth spray, paste dentifrice, clear gel dentifrice, mask, serum, solid cosmetic stick, lip balm, shampoo, liquid soap, bar soap, bath oil, paste, salve, collodion, impregnated patch, impregnated strip, skin surface implant, impregnated or coated diaper, and similar delivery or packaging form.

In another preferred aspect, the delivery system can be human body or hair deodorizing solution, deodorizing powder, deodorizing gel, deodorizing spray, deodorizing stick, deodorizing roll-on, deodorizing paste, deodorizing cream, deodorizing lotion, deodorizing aerosol, and other commonly marketed human body and hair deodorizing compositions, household deodorizing solution, deodorizing powder, deodorizing gel, deodorizing spray, carpet deodorizer, room deodorizer, and other commonly marketed household deodorizing compositions, animals and pets deodorizing solution, deodorizing powder, deodorizing gel, deodorizing spray, animals and pets carpet deodorizer, animals and pets room deodorizer, and other commonly marketed animal and pet deodorizing compositions.

In another preferred aspect, the delivery system can be traditional water and oil emulsions, suspensions, colloids, microemulsions, clear solutions, suspensions of nanoparticles, emulsions of nanoparticles, or anhydrous compositions.

Additional cosmetically or pharmaceutically beneficial ingredients can also be included in the formulated compositions of the present invention, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amylases, arabinans, arabinogalactans, arabinoxylans, carrageenans, gum arabic, carboxymethyl guar gum, carboxymethyl (hydroxypropyl) guar gum, hydroxyethyl guar gum, carboxymethyl cellulose, cationic guar gum, cellulose ethers including methyl cellulose, chondroitin, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, crosslinked dextrans, dextrin, emulsion, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer Encyclopedia of Chemical Technology, Fourth Edition, Vol. 16, John Wiley and Sons, NY pp. 578-611 (1994), which is incorporated entirely by reference. Complex carbohydrates found in Kirk-Othmer Encyclopedia of Chemical Technology, Fourth Edition, Vol. 4, John Wiley and Sons, NY pp. 930-948, 1995 which is herein incorporated by reference.

The cosmetically acceptable composition of this invention may include surface-active agents. Surface-active agents include surfactants, which typically provide detersive functionality to a formulation or act simply as wetting agents. Surface-active agents can generally be categorized as anionic surface-active agents, cationic surface-active agents, non-ionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, for example, sulfur trioxide or oleum, obtained according to known sulfonation methods, including bleaching and hydrolysis. Preferred are alkali metals and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecylbenzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL, as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowedimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowedimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include long chain fatty amines from about $C_{10}$ to $C_{22}$ and their derivatives. Specific examples include dipalmitylamine, lauramidopropyldimethylamine, and stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of the present invention, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH($CH_2$)$_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning, Midland, Mich., USA. Additional alkyl and phenyl silicones may be employed to enhance moisturizing properties. Resins such as dimethicone (and) trimethylsiloxysilicate or Cyclomethicone (and) Trimethylsiloxysilicate fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxyacetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, C.sub.12 to C.sub.16 fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane end blocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane-200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., and from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol. 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, Germany. When used, the silicone surfactants are preferably included in the formulations of this invention at a concentration of 0.1 to 30 weight percent, more preferably 1 to 15 weight percent. Amine functional silicones and emulsions may be utilized in the present invention. Preferred examples include Dow Corning 8220, Dow Corning 939, Dow Corning 949, Dow Corning 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the trade name Permethyl 101A, available from Presperse, South Plainfield, N.J., USA. Another example of a preferred volatile hydrocarbon is $C_{12}$ to $C_{14}$ isoparaffin, under the trade name Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17 Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers that can be used in this invention include high molecular weight crosslinked homopolymers of acrylic acid, and Acrylates/C10-30 Alkyl Acrylate Crosspolymer, such as the Carbopol and Pemulen series, both available from B.F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 20 weight percent, preferably 0.5 to 10 weight percent and most preferably from 1.0 to 5.0 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis(hydroxypropyl)aminobenzoate, 2-ethylhexyl 1-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD. Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT, Lonza, Fairlawn, N.J., USA, methylchloroisothiazolinone and methylisothiazolinone (e.g., Kathon, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerin, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, humectants, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, Carbopol-type acrylic acid thickeners available from B.F. Goodrich; xanthan gums; sodium alginates; gum arabic; cellulose derivatives and poly-(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

The cosmetic compositions of this invention may be formulated in a wide variety of form, for non-limited example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In detail, the cosmetic composition of the present invention can be provided in a form of skin softener (skin lotion), astringent lotion, nutrient emulsion (milk lotion), nutrient cream, message cream, essence, eye cream, cleansing cream, cleansing foam, cleansing water, facial pack, spray or powder.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonite, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane, butane, diethyl ether, or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension may comprise liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar and tragacanth or mixtures of these ingredients.

The formulation of cleansing compositions with surfactant may comprise aliphatic alcohol sulfate, aliphatic alcohol ether sulfate, sulfosucinnate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester or mixtures of these ingredients.

Additional antioxidant ingredients and compositions can be selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), .alpha.-Lipoic acid, Niacinamide lipoate, Glutathione, Andropropholide (*Andrographis paniculata*), Carnosine, Niacinamide, *Potentilla erecta* extract, Polyphenols, Grapeseed extract, Pycnogenol (Pine Bark extract), Pyridoxine, Magnolol, Honokiol, Paeonol, Resacetophenone, Quinacetophenone, arbutin, kojic acid, and combinations thereof.

The blood micro-circulation improvement ingredients and compositions can be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis Vinifera*) leaves, apigenin, phytosan, luteolin, and combinations thereof.

The anti-inflammatory ingredients or compositions can be selected from, but not limited to, at least one antioxidant class of Cyclo-oxygenase (for example, COX-1 or COX-2) or Lipoxygenase (for example, LOX-5) enzyme inhibitors such as Ascorbic acid, Ascorbic acid derivatives, Vitamin E, Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), alpha-Lipoic acid, Glutathione, Andropropholide, Grapeseed extract, Green Tea Extract, Polyphenols, Pycnogenol (Pine Bark extract), White Tea extract, Black Tea extract, (*Andrographis paniculata*), Carnosine, Niacinamide, and Emblica extract. Anti-inflammatory composition can additionally be selected from, but not limited to, Horse Chestnut Extract (*Aesculus hippocastanum* extract)), Esculin, Escin, Yohimbine, *Capsicum* Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Sericoside, Visnadine, Thiocolchicoside, Grapeseed Extract, Ginger Root Extract (*Zingiber Officianalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), *Amni visnaga* extract, extract of Red Vine (*Vitis-Vinifera*) leaves, apigenin, phytosan, luteolin, and combinations thereof.

Certain divalent and polyvalent metal ions can also be present in the compositions of the present invention. The examples of such metal ions include zinc, copper, manganese, vanadium, chromium, cobalt, and iron.

The present invention also provides a pharmaceutical composition that comprises a carrier and, as active ingredient, a compound of the general formula (VII) as defined above.

A pharmaceutically acceptable carrier may be any material with which the active ingredient is formulated to facilitate administration. A carrier may be a solid or a liquid, including a material that is normally gaseous but which has been compressed to form a liquid, and any of the carriers normally used in formulating pharmaceutical compositions may be used. Preferably, compositions according to the invention contain 0.5 to 95% by weight of active ingredient.

The compounds of general formula (VII) can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

For treatment of and prophylaxis against coccidiosis and related parasites, for instance, in poultry, especially in chickens, ducks, geese and turkeys, 0.1 to 100 ppm, preferably 0.5 to 100 ppm of the active compound may be mixed into an appropriate, edible material, such as nutritious food. If desired, the amounts applied can be increased, especially if the active compound is well tolerated by the recipient. Accordingly, the active compound can be applied with the drinking water.

For the treatment of a single animal, for instance, for the treatment of coccidiosis in mammals or toxoplasmosis, amounts of 0.5 to 100 mg/kg body weight active compound are preferably administered daily to obtain the desired results. Nevertheless, it may be necessary from time to time to depart from the amounts mentioned above, depending on the body weight of the experimental animal, the method of application, the animal species and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses.

The present invention also includes a compound of the general formula (VII) as defined above for use in the treatment and/or prophylaxis of a disease caused by infection with a parasite of the genus *Plasmodium* and use of a compound of the general formula (VII) as defined above for the manufacture of a medicament for the treatment and/or prophylaxis of a disease caused by infection with a parasite of the genus *Plasmodium*.

The invention also provides a method for treating a disease caused by infection with a parasite other than an organism of the genus *Plasmodium* that comprises administering to a host in need of such treatment a therapeutically effective amount of a compound of the general formula (VII) as first defined above. Preferably, the parasite is an organism of the genus Neospora or the genus *Eimeria*. A method for treating a disease caused by infection with a parasite of the genus *Plasmodium* is also provided which comprises administering to a host in need of such treatment a therapeutically effective amount of a novel compound of the general formula I as defined above.

EXAMPLES

All quantities are in weight percent amounts. The examples do not limit the scope of the present invention. Nomenclature of some compounds has been abbreviated.

Example 1

Preparation of N-(Decanoyl)-Glutaminyl-Glutamine Amide (Formula IV)

Procedure. An equimolar amount of glutaminyl-glutamine amide, sodium bicarbonate, and decanoyl chloride are reacted in water. The pH is adjusted to 5.5 to 6.5, whereupon compound of formula (IV) crystallizes out, which is then filtered, washed with water, and dried.

Example 2

Preparation of Glutaminyl-Glutamine Amide (Formula V)

Procedure. Glutaminyl-glutamine amide (formula V) is obtained by standard peptide synthesis.

Example 3

Preparation of N-Acetyl-Glutamyl-Glutamic Acid (Formula VIII)

Procedure. An equimolar amount of glutamyl-glutamic acid, sodium bicarbonate, and acetyl chloride are reacted in water. The pH is adjusted to 5.5 to 6.5, whereupon compound of formula (VIII) crystallizes out, which is then filtered, washed with water, and dried.

Example 4

Skin Whitening and Anti-Wrinkle Serum

Ingredients. (1) Ethyl Lactate 24.0 (2) Polyalkyleneoxy Polyamide 0.5 (3) Compound of formula (VII) 1.0 (4) PEG-670.0 (5) Resacetophenone 4.0 (6) Preservatives 0.5. Procedure. Make serum base by mixing (1) to (3) at room temperature or slight heating. Pre-mix (4) to (6) to a clear solution and add to main batch with mixing. The product has serum like appearance.

Example 5

Anti-Acne and Facial Oil Control Cream

Ingredients. (1) Deionized water 79.5 (2) Cetearyl alcohol (and) dicetyl phosphate (and) Ceteth-10 phosphate 5.0 (3) Cetyl alcohol 2.0 (4) Glyceryl stearate (and) PEG-100 stearate 4.0 (5) Ethyl Lactate 5.0 (6) Compound of formula (IV) 3.0 (7) N-(Deoxyaloesinylideneamino)-4-hydroxyphenylacetic acid 1.0 (8) Preservatives 0.5. Procedure. Mix 1 to 5 and heat to 75-80.degree. C. Adjust pH to 4.0-4.5. Cool to 35-40 C with mixing. Add 6 to 8 with mixing. Adjust pH to 4.0-4.5, if necessary. An off-white cream is obtained.

Example 6

Skin Abrasion Treatment Cream

Ingredients. (1) Water 53.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Water 5.0 (15) Niacinamide Lactate 1.0 (16) Niacinamide Hydroxycitrate 3.1 (17) Compound of formula (V) 2.5 (18) Paeonol 1.5 (19) Carnosine 0.1 (20) Cyclomethicone, Dimethicone Crosspolymer 2.0 (21) Arbutin 0.5 (22) Polysorbate-20 2.0 (23) Ethyl Lactate 12.0. Procedure. Mix (1) to (13) and heat at 70 to 80 C till homogenous. Cool to 40 to 50C. Premix (14) to (16) and add to batch with mixing. Mix (17) to (23) to a clear solution and add to main batch mix. Cool to room temperature. An off-white cream is obtained.

Example 7

Acne Cream

Ingredients. (1) Water 53.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Niacinamide Hydroxycitrate 2.2 (15) Ethyl Lactate 15.0 (16) Niacinamide Salicylate 4.0 (17) Compound of formula (V) 1.1 (18) Paeonol 1.5 (19) Carnosine 0.1 (20) Cyclomethicone, Dimethicone Crosspolymer 2.0 (21) Arbutin 0.5 (22) Salicylic Acid 2.0 (23) Polysorbate-20 2.0 (24) Polyacrylamide 2.0. Procedure. Mix (1) to (15) and heat at 70 to 80 C till homogenous. Cool to 40 to 50 C. Premix (16) to (23) and heat, if necessary, to a solution and add to main batch with mixing. Cool to room temperature and add (24) and mix. An off-white cream is obtained.

Example 8

Pet Cleanser

Ingredients. (1) PEG-6 47.229 (2) Hydroxypropyl Guar 0.4 (3) Sodium Cocoyl Isethionate 20.0 (4) Sodium Lauryl Sulfoacetate 5.0 (5) *Boswellia Serrata* 0.05 (6) L-Glutathione 0.01 (7) Resveratrol 0.01 (8) Compound of formula (VII) 1.1 (9) 2,6-Dihydroxy Acetophenone 0.001 (10) Ascorbic acid 10.0 (11) Phenoxyethanol 0.7 (12) Ethylhexylglycerin 0.3 (13) Fragrance 0.2 (14) Ethylhexyl Lactate 15.0. Procedure. Mix (1) and (2) to a clear thin gel. Add (3) and (4) and mix. Premix (5) to (14) to a solution. Add to main batch and mix. A white cream-like cleanser is obtained.

Example 9

Anti-Inflammatory Transparent Gel for Veterinary Use

Ingredients. (1) Ethyl Lactate 96.0 (2) Hydroxypropyl Guar 1.0 (3) Ximenia Oil 0.1 (4) N-(Deoxyaloesinylideneamino)-4-hydroxyphenylacetic acid (from Example 13) 1.0 (5) Magnolol (and) Honokiol 0.2 (6) Paeonol 0.5 (7) Compound of formula (VII) 0.2 (8) Fragrance 1.0. Procedure. Mix (1) and (2) and heat at 50 to 60 C till clear. Cool to 40 to 45 C and add all other ingredients and mix. Cool to room temperature. A transparent gel-like product is obtained.

Example 10

Heat Releasing Face and Body Skin Brightening Cleanser

Ingredients. (1) Ethyl Lactate 5.0 (2) Hydroxypropyl Guar 0.4 (3) PEG-6 36.9 (4) Glycerin 2.0 (5) Vitamin E 0.1 (6) Botanicals blend 0.1 (7) Zeolite 30.0 (8) Disodium Lauryl Sulfosuccinate powder 7.5 (9) Sodium Cocoyl Isethionate powder 11.0 (10) Shea butter 1.1 (11) Apricot Kernel Oil 0.5 (12) Compound of formula (VIII) 1.1 (13) Mango butter 0.5 (14) Fragrance 3.0 (15) Preservative 0.8. Procedure. Mix (1) to (3) and heat at 40 to 50 C till a clear gel is obtained (about one hour). Pre-mix (4) to (6) and add to main batch and mix. Add (7) to (13) and mix. Cool to 35 to 45 C. Add all other ingredients to main batch and mix. Cool to room temperature to an off-white paste. Upon application to slightly wet face or body, heat release is experienced and voluminous foam is generated upon rubbing skin with some more water.

Example 11

Facial Glow Serum

Ingredients. (1) Butylene Glycol 57.9 (2) Water 10.0 (3) Ascorbic Acid 10.0 (4) Diglycerol 10.0 (5) Bis-PEG-18 Methyl Ether Dimethyl Silane 4.0 (6) Acrylates/Aminoacrylates/C-10-30 Alkyl PEG-20 Itaconate Copolymer 4.0 (7) Compound of formula (VII) 1.5 (8) Glycine 1.0 (9) Magnolol 0.2 (10) Baicalin 0.2 (11) Coleus Forskohlii Root Extract 0.1 (12) Preservative 1.0. Procedure. Make Premix A by mixing (2), (7), and (8) at 60 to 70 C for 30 min., then add (3) with mixing. Make Premix B by mixing all other ingredients, except (6), separately. Mix Premix A and Premix B, then add (6) with mixing to adjust viscosity.

Example 12

Facial Glow Cream

Ingredients. (1) Water 72.45 (2) Dicetyl phosphate and Ceteth-10 phosphate 5.0 (3) Glyceryl Stearate and PEG-100 stearate 4.0 (4) Diglycerol 2.0 (5) Shea butter 2.0 (6) Aloesin 1.5 (7) Compound of formula (VII) 2.2 (8) Capuacu butter 1.0 (9) Sodium hydroxide 0.25 (10) *Boswellia serrata* extract 0.5 (11) Tetrahydrocurcumin 0.2 (12) Paeonol 0.2 (13) Arbutin 1.1 (14) Coleus Forskohlii Root extract 0.1 (15) Polysorbate-20 4.0 (16) Carnosine 0.1 (17) Preservative 1.0 (18) Polyacrylamide and C13-14 Isoparaffin and Laureth-7 2.0. Procedure. Make Premix A by mixing (1), (6), and (7) at 80 to 90 C. Add all other ingredients and continue mixing until homogenous. Cool to room temperature.

Example 13

Dandruff Cleanser Shampoo

Ingredients. (1) Water 52.5 (2) *Artemisia annua* extract 1.5 (3) Glycine 1.0 (4) Arbutin 0.5 (5) Magnolol 0.2 (6) Coleus Forskohlii Root Extract 0.3 (7) Preservative 1.0 (8) Compound of formula (XII; R=H) 1.0 (9) Sodium Methyl Cocoyl Taurate 20.0 (10) Sodium Cocoyl Isethionate 20.0 (11) PEG-120 Methyl Glucose Dioleate 2.0. Procedure. Mix (1) to (3) at 80 to 90 C. Add all other ingredients. Continue mixing until homogenous. Cool to room temperature.

Example 14

High Foaming Pet Cleanser for Veterinary Use

Ingredients. (1) Water 51.4 (2) 1.5 (3) Zinc Salicylate Glycinate 2.1 (4) Paeonol 0.5 (5) Magnolol 0.2 (6) Coleus Forskohlii Root Extract 0.3 (7) Preservative 1.0 (8) Compound of formula (XII; R=H) 1.0 (9) Sodium Methyl Cocoyl Taurate 20.0 (10) Sodium Cocoyl Isethionate 20.0 (11) PEG-120 Methyl Glucose Dioleate 2.0. Procedure. Mix (1) to (11) at 80 to 90 C. Continue mixing until homogenous. Cool to room temperature.

Example 15

Rosacea Cream

Ingredients. (1) Water 53.9 (2) Dicetyl Phosphate (and) Ceteth-10 Phosphate 5.0 (3) Glyceryl Stearate (and) PEG-100 Stearate 4.0 (4) Phenoxyethanol 0.7 (5) Chlorphenesin 0.3 (60) Titanium Dioxide 0.2 (7) Sodium Hydroxide 0.5 (8) Magnolol 0.2 (9) *Boswellia Serrata* 0.5 (10) Cetyl Dimethicone 1.5 (11) Tetrahydrocurcuminoids 0.5 (12) Shea butter 2.0 (13) Ximenia oil 1.0 (14) Niacinamide Hydroxycitrate 2.2 (15) Ethyl Lactate 15.0 (16) Niacinamide Salicylate 4.0 (17) *Artemisia annua* extract 10.1 (18) Paeonol 1.5 (19) Carnosine 0.1 (20) Cyclomethicone, Dimethicone Crosspolymer 2.0

(21) Compound of formula (XI; R=H) 0.5 (22) Salicylic Acid 2.0 (23) Polysorbate-20 2.0 (24) Polyacrylamide 2.0. Procedure. Mix (1) to (15) and heat at 70 to 80 C till homogenous. Cool to 40 to 50 C. Premix (16) to (23) and heat, if necessary, to a solution and add to main batch with mixing. Cool to room temperature and add (24) and mix. An off-white cream is obtained.

Enzyme Inhibition Test

A simple test to evaluate enzyme inhibition activity of the compounds of the present invention was done. A solution of compound from Example 1 (0.1%) in warm water (to effect solubilization) was allowed to come in contact with a suspension of an enzyme in phosphate buffer and the inhibition was observed. The results are summarized in Table 1.

TABLE 1

| Enzyme Inhibition Test. | |
| --- | --- |
| Enzyme | Inhibition |
| Tyrosinase | + |
| Matrix Metalloproteases | + |
| Phenylalanine Oxidase | + |
| Catalase | + |
| Collagenase | + |
| Elastase | + |

The invention claimed is:

1. A composition comprising a compound; wherein, said compound is selected from the group consisting of:

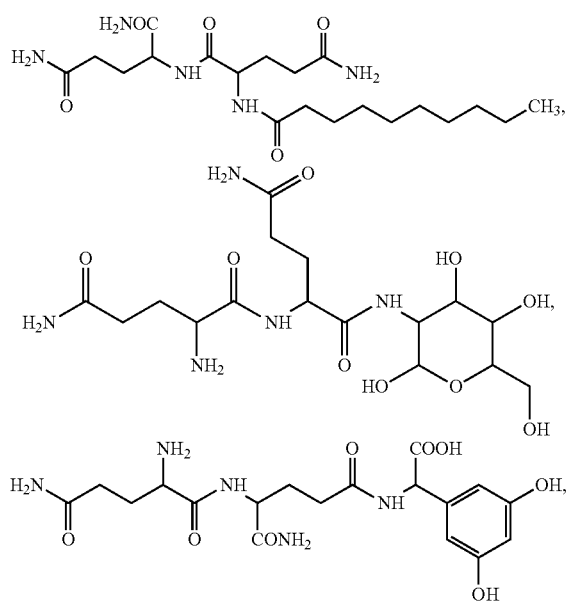

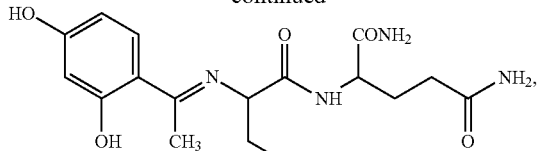

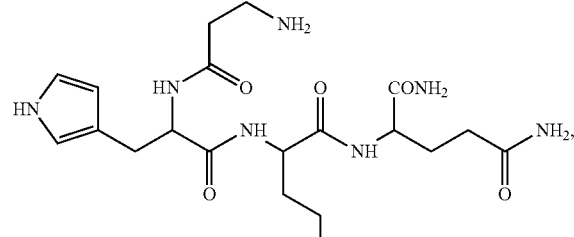

and

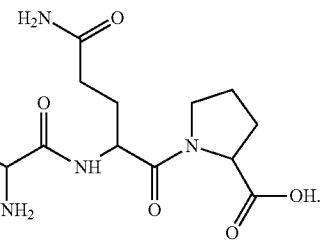

2. A composition of claim 1 for treatment of a condition of skin degradation, wherein said condition is selected from a group consisting of: cancer, diabetes, radiation treatments, chemotherapy, and sun-burn; mitochondrial dysfunction, age spots, acne, loss of cellular antioxidants, collagen loss, loss of skin pliability, loss of skin suppleness, skin wrinkles including fine lines, oxidation, damage from radiation, damage from free radicals, damage from UV, dry skin, xerosis, ichthyosis, dandruff, brownish spots, keratoses, melasma, lentigines, liver spots, pigmented spots, dark circles under the eyes, skin pigmentation including darkened skin, blemishes, oily skin, warts, eczema, pruritic skin, psoriasis, inflammatory dermatoses, topical inflammation, disturbed keratinization, skin changes associated with aging, scalp dryness, skin depigmentation, intracellular dehydration, and combinations thereof.

3. A composition comprising said salt of a compound of claim 1, wherein said salt is a metal salt; said metal is selected from the group consisting of Li, Na, K, Ca, Mg, Ti, V, Cr, Mn, Fe, Co, Ni, Cu, Zn and Se.

4. A composition comprising said salt of a compound of claim 1, wherein said salt is an acid salt; said acid is selected from the group consisting of inorganic and organic acids.

5. A composition comprising a compound of claim 1 for pharmaceutical, nutraceutical, cosmetic, topical, or oral application.

6. A composition of claim 2, wherein said condition of skin degradation is wrinkles and fine lines.

* * * * *